United States Patent
Raizada

(10) Patent No.: US 9,276,938 B2
(45) Date of Patent: Mar. 1, 2016

(54) CROSS-ENTERPRISE WORKFLOW

(71) Applicant: General Electric Company, Schenectady, NY (US)

(72) Inventor: Piyush Raizada, Barrington, IL (US)

(73) Assignee: General Electric Company, Schenectady, NY (US)

( * ) Notice: Subject to any disclaimer, the term of this patent is extended or adjusted under 35 U.S.C. 154(b) by 80 days.

(21) Appl. No.: 14/092,764

(22) Filed: Nov. 27, 2013

(65) Prior Publication Data
US 2015/0150092 A1   May 28, 2015

(51) Int. Cl.
G06F 21/00  (2013.01)
H04L 29/06  (2006.01)
G06F 19/00  (2011.01)

(52) U.S. Cl.
CPC .............. *H04L 63/10* (2013.01); *G06F 19/321* (2013.01); *G06F 19/322* (2013.01); *G06F 19/327* (2013.01); *H04L 63/08* (2013.01)

(58) Field of Classification Search
CPC .................................................. H04W 12/06
See application file for complete search history.

(56) References Cited

U.S. PATENT DOCUMENTS

| | | | |
|---|---|---|---|
| 6,584,454 B1 * | 6/2003 | Hummel et al. | 705/59 |
| 2004/0268364 A1 * | 12/2004 | Faraj | 719/316 |
| 2006/0080430 A1 * | 4/2006 | Barsuk | 709/224 |
| 2006/0248554 A1 * | 11/2006 | Priddy | 725/25 |
| 2008/0177569 A1 * | 7/2008 | Chen et al. | 705/2 |
| 2009/0106823 A1 * | 4/2009 | Durski | 726/4 |
| 2010/0100970 A1 * | 4/2010 | Roy-Chowdhury et al. | 726/30 |
| 2010/0318992 A1 * | 12/2010 | Kushwaha et al. | 718/1 |
| 2014/0240326 A1 * | 8/2014 | Cutter et al. | 345/502 |

OTHER PUBLICATIONS

Bojan Blazona et al., "HL7 and DICOM based integration of radiology departments with healthcare enterprise information systems", International Journal of Medical Informatics, Jan. 7, 2007, 8 pages.

* cited by examiner

*Primary Examiner* — Lisa Lewis
(74) *Attorney, Agent, or Firm* — Hanley, Flight and Zimmerman, LLC

(57) ABSTRACT

Example systems, methods and storage media to provide a cross-enterprise workflow among clinical systems are disclosed. An example cross-enterprise enabled clinical information system includes a workflow manager to coordinate user workflows with respect to the system and associated content. The system includes an image services manager configured to manage images and associated services for the system and associated content. The workflow manager and image services manager are configured for cross-enterprise content sharing such that the system is to locally authenticate a user at the system and the system is to locally authorize a remote request for access to content at the system from a remote user that has been authenticated remotely. The system is arranged to provide content in response to the remote request after the remote authentication has been received and the system has verified the remote user's authorization for access.

18 Claims, 26 Drawing Sheets

CROSS-ENTERPRISE WORKFLOW

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

Healthcare practitioners may review medical exam results stored in information systems such as hospital information systems (HIS), radiology information systems (RIS), clinical information systems (CIS), cardiovascular information systems (CVIS, etc., and storage systems such as picture archiving and communication systems (PACS), library information systems (LIS), and electronic medical records (EMR). Information stored can include patient medication orders, medical histories, imaging data, test results, diagnosis information, management information, and/or scheduling information, for example. The healthcare practitioners may obtain the information from information systems included in the healthcare environment, such as hospitals or clinics, in which the practitioner practices (e.g., local information systems) or from information systems included in other healthcare environment(s) (e.g., foreign or remote information system(s)).

BRIEF SUMMARY

Example systems, methods and tangible computer readable storage media to provide a cross-enterprise workflow among clinical systems are disclosed and described.

Certain examples provide a cross-enterprise enabled clinical information system. The example system includes a workflow manager to coordinate user workflows with respect to the system and associated content. The example system also includes an image services manager configured to manage images and associated services for the system and associated content. The example workflow manager and image services manager are configured for cross-enterprise content sharing such that the system is to locally authenticate a user at the system and the system is to locally authorize a remote request for access to content at the system from a remote user that has been authenticated remotely. The example system is arranged to provide content in response to the remote request after the remote authentication has been received and the system has verified the remote user's authorization for access. At least one of the workflow manager and the image services manager is to provide content to the remote user depending upon a type of requested content.

Certain examples provide a tangible computer readable storage medium including instructions which, when executed, implement a cross-enterprise enabled clinical information system. The example system includes a workflow manager to coordinate user workflows with respect to the system and associated content. The example system also includes an image services manager configured to manage images and associated services for the system and associated content. The example workflow manager and image services manager are configured for cross-enterprise content sharing such that the system is to locally authenticate a user at the system and the system is to locally authorize a remote request for access to content at the system from a remote user that has been authenticated remotely. The example system is arranged to provide content in response to the remote request after the remote authentication has been received and the system has verified the remote user's authorization for access. At least one of the workflow manager and the image services manager is to provide content to the remote user depending upon a type of requested content.

Figure 1:
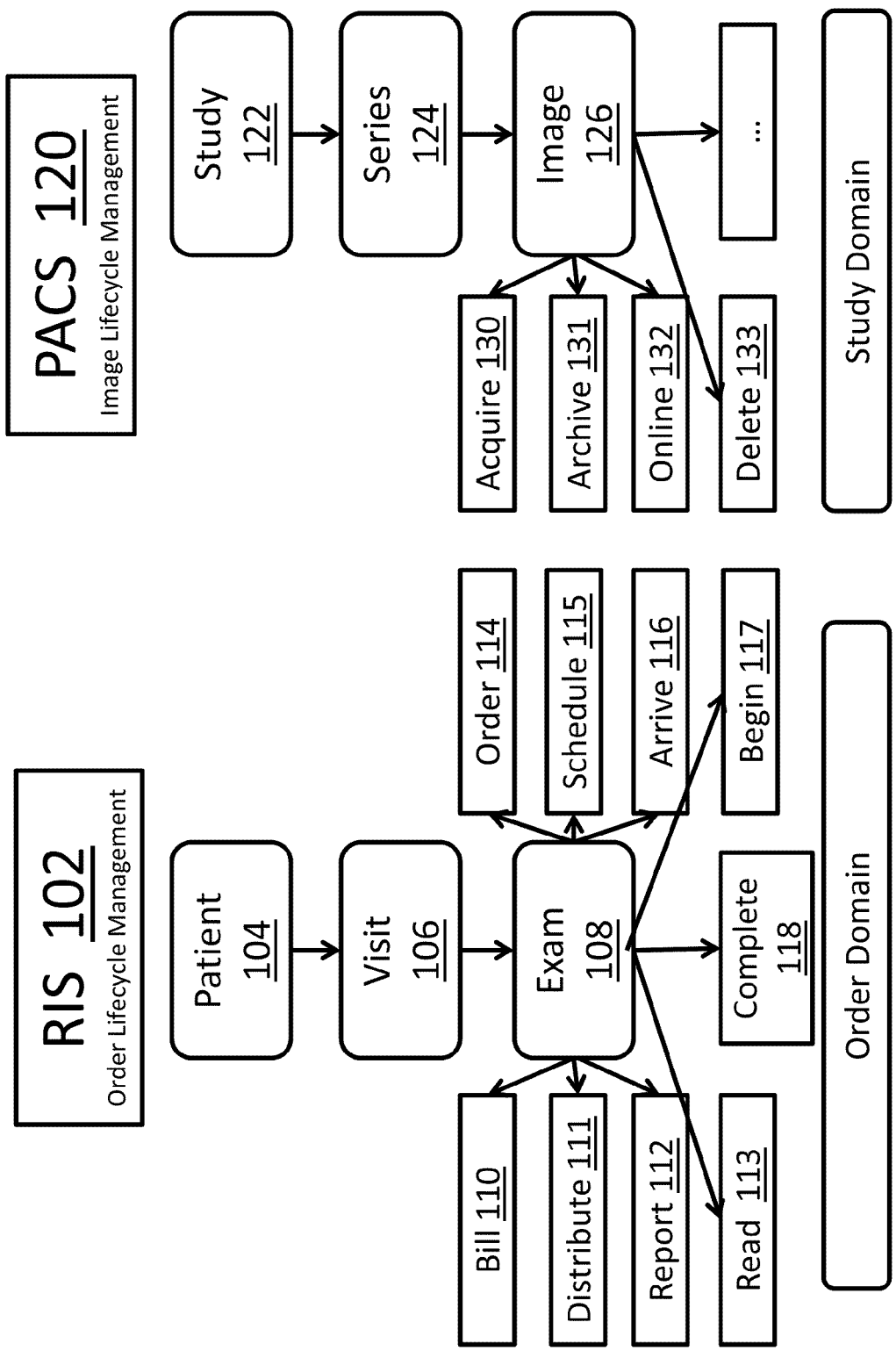
FIG. 1 illustrates example RIS and PACS providing order lifecycle management (via the RIS) and image lifecycle management (via the PACS).

The foregoing summary, as well as the following detailed description of certain examples of the present invention, will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF CERTAIN EMBODIMENTS

Although the following discloses example methods, systems and computer readable media including, among other components, software and/or firmware executed on hardware, it should be noted that such methods and apparatus are merely illustrative and should not be considered as limiting. For example, it is contemplated that any or all of these hardware, software, and firmware components could be embodied exclusively in hardware, exclusively in software, or in any combination of hardware and software. Accordingly, while the following describes example methods, systems, and computer readable media, persons of ordinary skill in the art will readily appreciate that the examples provided are not the only way to implement such methods, systems and computer readable media.

The present disclosure relates generally to healthcare applications, and, more particularly, to methods, systems, and apparatus to provide integrated workflow and image services via standalone and/or cross-enterprise system configurations.

Many healthcare environments include radiology information systems to facilitate patient examination and/or patient diagnosis. For example, a radiology information system in a healthcare system can store radiology reports, messages, warning, alerts, patient scheduling information, patient demographic data, patient tracking information, and/or physician and patient status monitors.

Typically, a medical exam ordered for a patient is assigned to a practitioner (e.g., a radiologist) to conduct the exam. A medical exam conducted on a patient can involve review by a healthcare practitioner (e.g., a radiologist) to obtain, for example, diagnostic information from the exam. In a hospital setting, medical exams can be ordered for a plurality of patients, all of which involve review by an examining practitioner. Each exam may have associated attributes, such as a modality, a part of the human body under exam, and/or an exam priority level related to a patient criticality level. In some examples, however, not all the information needed for reviewing a medical exam is locally available. For example, a practitioner (e.g., a radiologist or a technician) may want to review information about a patient, but the information may be spread across different information systems.

In some systems, the practitioner may review printouts of the information from the different information systems. However, the printouts may not include up-to-date information. For example, information in an information system may be updated to include a new resting heart rate for the patient. In some systems, the practitioner may access the information from the different information systems by manually connecting to each of the necessary information systems. This cumbersome process of logging into an information system whenever information from that information system is needed can cause the practitioner to obtain the information less frequently. Thus, the practitioner may review the medical exam (or record) for the patient with stale information.

In some systems, a healthcare institution builds a unified system that includes all the data from the different information systems. For example, the unified system can populate the unified system with all the information stored in a first hospital information system, a second hospital information system, a radiology information system, etc. Such unified systems necessitate large databases to store all of the information. Further, transforming the information (e.g., cleansing, reformatting, standardizing, aggregating and/or applying any number of business rules) from the different information systems into a single format as needed for the unified system can be impractical. For example, each of the different information systems may be controlled by different business rules or service level agreements, store the information in different formats, include different definitions for optional elements versus required elements, etc. In addition, if the information is transformed at the unified system, returning the data (e.g., information updated by the practitioner) to the source information system can be unreasonable.

Disclosed and described herein are example systems, methods and computer readable media that provide for integration between a radiology information system (RIS) and a picture archiving and communication system (PACS) according to a single data schema. A schema is a structure described according to a language and/or other format to provide one or more formula, format, integrity constraint, relationship, attribute, rule, etc., to organize, relate, process, and/or store information.

Using single schema-based integration, certain examples facilitate operation with a plurality of workflow back-ends. Unlike other solutions which require integration between disparate systems/sub-systems, certain examples abstract and extract domain specific entities into updatable database views. A new application is then constructed on top of this schema. The new application is agnostic to the underlying database structure (that belongs to one or more existing products).

Certain examples provide a "bolt-on approach" allowing for immediate use of existing data by the new application without synchronization. Certain examples use Extract, Transform, Load (ETL) to extract data from outside sources, transform the extracted data to fit operational needs, and load the transformed data into an end target data store. Certain examples reduce install/upgrade time and service costs by reducing or eliminating ETL in accordance with the single schema. Certain examples facilitate these operations via the new application while the existing base application continues to function as before, oblivious to another (e.g., competing) application (e.g., the "new" application) working on the same schema/dataset. This allows customers to slowly transition from an existing application to the new and different application while not suffering from data migration to do so.

In certain examples, a hospital information system (HIS) stores medical information such as clinical reports, patient information, and/or administrative information received from, for example, personnel at a hospital, clinic, and/or a physician's office. A RIS stores information such as, for example, radiology reports, radiology exam image data, messages, warnings, alerts, patient scheduling information, patient demographic data, patient tracking information, and/or physician and patient status monitors. Additionally, the RIS enables exam order entry (e.g., ordering an x-ray of a patient) and image and film tracking (e.g., tracking identities of one or more people that have checked out a film). In some examples, information in the RIS 106 is formatted according to the HL-7 (Health Level Seven) clinical communication protocol. In certain examples, a medical exam distributor is located in the RIS to facilitate distribution of radiology exams to a radiologist workload for review. In an alternative example, the exam distributor can be located separately or can be included in any other suitable device of the healthcare system.

A PACS stores medical images (e.g., x-rays, scans, three-dimensional renderings, etc.) as, for example, digital images in a database or registry. In some examples, the medical images are stored in the PACS using the Digital Imaging and Communications in Medicine ("DICOM") format. Images are stored in the PACS by healthcare practitioners (e.g., imaging technicians, physicians, radiologists) after a medical imaging of a patient and/or are automatically transmitted from medical imaging devices to the PACS for storage. In some examples, the PACS can also include a display device and/or viewing workstation to enable a healthcare practitioner or provider to communicate with the PACS.

Diagnostic and medical image processing solutions such as PACS and RIS help to drive and support digital images and patient data through improved image storage, viewing, sharing and retrieval, resulting in an improvement in workflow efficiency and productivity. Such improvements are of growing importance as the world population ages and co-morbidities increase demand for medical imaging and analytics and a resulting need for image processing and management for large volumes of data.

Additionally, PACS have evolved from a tool for medical image viewing, distribution, and archiving into a system supporting clinical decision making. PACS can include advanced visualization tools, voice recognition solutions, customized worklists, teleradiology, cloud-based PACS, zero-footprint viewers, and mobile PACS, for example. PACS may be integrated with three-dimensional (3D) 3D visualization, maximum intensity projection (MIP), and multi-planar reformation (MPR) tools, for example.

In certain examples, Vendor-Neutral Archiving (VNA) can be used in place of and/or in addition to a PACS for image archiving and/or other storage. Using a VNA, a plurality of different PACS and/or other different systems can store and retrieve images without translation or transformation at the VNA. An enterprise archive (EA) can also be used within an enterprise to storage and later retrieve image and/or other data, for example.

RIS/PACS Relationships

Turning now to the figures, FIG. 1 illustrates example RIS 102 and PACS 120 providing order lifecycle management (via the RIS 102) and image lifecycle management (via the PACS 120). As depicted in the example of FIG. 1, the RIS 102 is an order lifecycle management system. That is, the RIS 102 is an order filler. The RIS 102 works in an order domain where an order is a center of focus and activity. As depicted in the example of FIG. 1, the PACS 120 is an image lifecycle management system. The PACS 120 works in a study domain where an image is a center of focus and activity.

The order and image domains do not overlap and do not compete in a workflow. Rather, the domains are complementary and in lock step. A larger departmental workflow encompasses both the RIS 102 and the PACS 120.

As shown in the example of FIG. 1, the RIS 102 documents a patient 104 who has one or more visits 106 that may include one or more exams 108. One or more actions 110-118 can be executed and documented with respect to the exam 108. For example, the exam can be billed 110, distributed 111, reported 112, read 113, ordered 114, scheduled 115, patient arrival 116, started 117, completed 118, etc.

As shown in the example of FIG. 1, the PACS 120 documents a study 122 including one or more series 124 of one or more images 126. Each image 126 can be acquired 130, archived 131, made available online 132, deleted 113, etc., via the PACS 120, for example.

Figure 2:
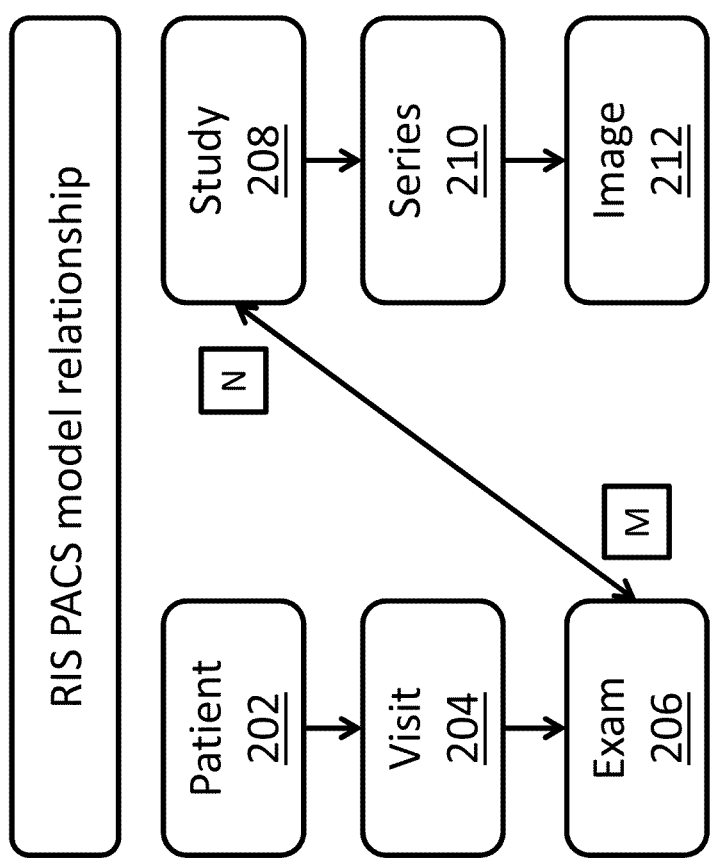
FIG. 2 illustrates an example relationship between a RIS and a PACS.

FIG. 2 illustrates an example relationship between a RIS and a PACS. As illustrated in the example of FIG. 2, a radiologist reads an exam by retrieving exam information 206 from a visit 204 for a patient 202 from the RIS and information on an image 212 from a series 210 in a study 208 from the PACS. A report is generated by the radiologist and stored in the RIS. Additionally, a technologist can edit one or more studies 208 in the PACS as well as one or more exams 206 in the RIS. Exception handling can be provided in both the RIS and the PACS, for example. A radiology administrator can also edit or more studies 208, exams 206, etc.

By combining and/or otherwise tightening a relationship between the RIS and the PACS, a usability experience can be improved for a radiologist, technologist, radiology administrator, and so on. Certain examples provide a single (e.g., seamless or substantially seamless) user interface that allows users to perform their work regardless of whether the work impacts the RIS and/or PACS. In certain examples, an order lifecycle manager can be provided with an image viewer, while image lifecycle management (traditionally handled by the PACS) is left to an EA.

The order domain model and the image domain model are related by a single relationship between the exam 206 (e.g., accession number) and the study 208 (e.g., study instance unique identification number (UID)). Further, exam 206 and study 208 are related by an M:N relationship. One exam 206 can be associated with more than one study 208 and vice versa. A practical relationship is between an exam 206 and one or more series 210.

Example RIS/PACS Integration

Figure 3:
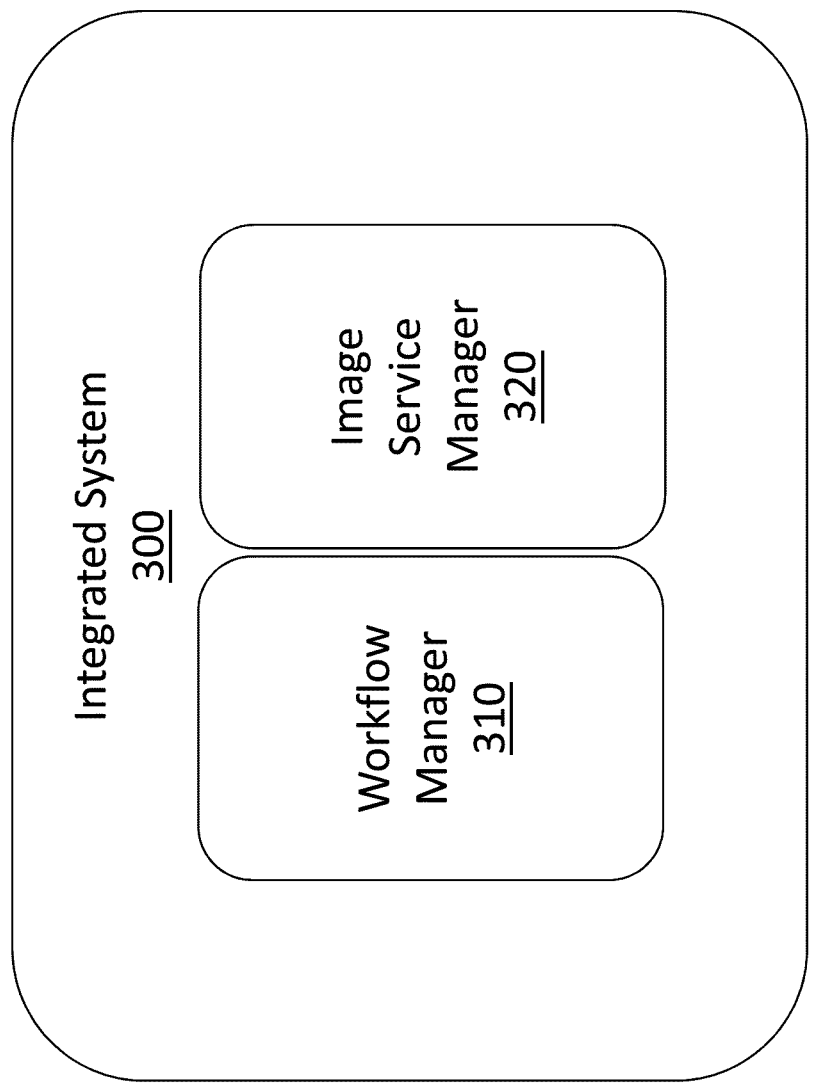
FIG. 3 shows a high level view of an example integrated system including a workflow manager and an image service manager.

FIG. 3 shows a high level view of an example integrated system 300 including a workflow manager 310 and an image service manager 320. As illustrated in the high-level system view 300, traditional RIS and PACS functionality can be replaced by the workflow manager 310 working together with the image service manager 320. Images and associated services can be managed by the image service manager 320 while the workflow manager 310 coordinates user workflows (e.g., radiologist workflow, technologist workflows, administrator workflows, etc.).

Figure 4:
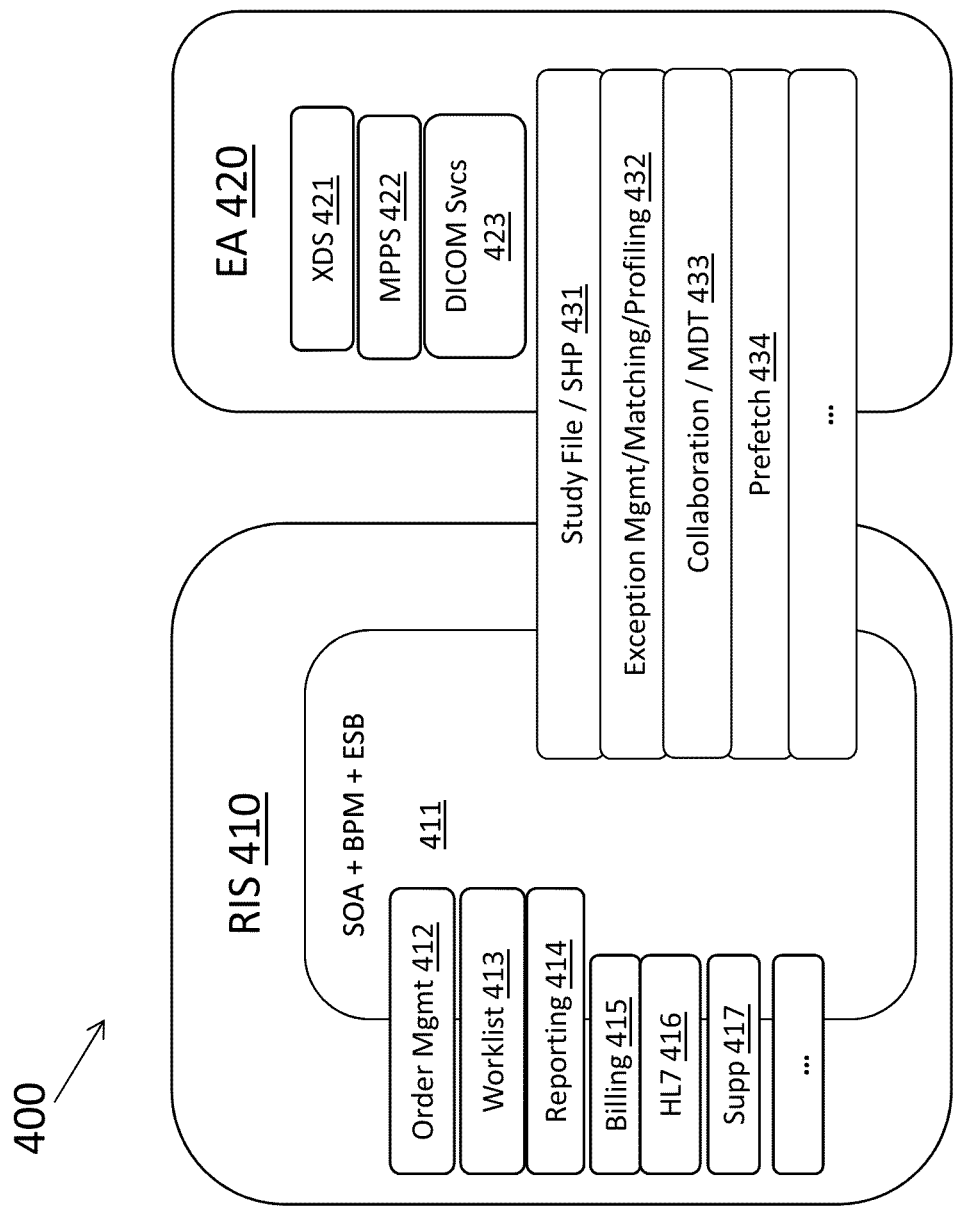
FIG. 4 illustrates an example backend for an integrated clinical information system.

FIG. 4 illustrates an example backend 400 for an integrated clinical information system. The example system 400 includes a RIS 410 and an EA 420. As illustrated in the example of FIG. 4, while functionality crosses domains (e.g., study file/smarting hanging protocol (SHP) 431 (SHP may also be referred to as a smarting reading protocol, for example), exception management/matching/profiling 432, collaboration/multidisciplinary team (MDT) 433, prefetch 434, etc.), services do not cross domains (e.g., order management 412, worklist 413, reporting 414, billing 415, messaging (e.g., HL7) 416, support 417, cross-enterprise document sharing (XDS) 421, modality performed procedure step (MPPS) 422, Digital Imaging and Communications in Medicine (DICOM) services 423, etc.). Thus, while functionality may still have separate modules and components are oblivious to each other in the architecture, they can function together in the same system.

The RIS 410 can also include a combination of service-oriented architecture (SOA), business process management (BPN), and an enterprise service bus (ESB) 411, for example. Web services can be used provide isolation and/or separation between PACS and RIS 410 to reduce the system's regulatory footprint, for example. In certain examples, a single database schema can be used to support functionality from a PACS that may otherwise be missing in the integrated system 400 including RIS 410 and EA 420.

Single Schema-Based RIS/PACS Integration

Certain examples provide a true combined RIS/PACS system. One schema provides one definition of a patient, an order, a visit, etc., that is shared by both RIS and PACS functionality. While prior approaches use different RIS and PACS schema, certain examples provide one schema to use with a patient for both PACS and RIS data. Certain examples use a same schema and same middle tier for both RIS and PACS applications. Certain examples leverage the single schema for any combination of RIS/PACS, RIS, PACS, worklist, etc., as various configurations of the same code.

In certain examples, as separate systems are collapsed into a single system, performance can be improved in certain areas. For example, data can be modeled after caching. Information normally pulled at runtime from different sources can be pulled up from into a digest that is available when needed.

As discussed above and disclosed and described further below, one or more of the HIS, RIS, PACS, and/or other clinical system can be integrated for single schema operation over multiple back-ends. In certain examples, each system includes two types of objects, as persisted in a database. One type of object is "Objects of Domain", such patient, exam, visit, etc., which are modeled after one or more real world entities and, though an implementation/model may vary from system to system, the information at a certain abstraction level does not vary with objects of domain. Such objects can be re-modeled using updatable views or other such mechanisms. Other objects are "Objects of Design" that are specific to the functioning of an application. These objects vary from application to application.

Certain examples provide an abstracted data model of a healthcare domain that works on a variety of healthcare information system platforms. Applications can be developed on top of this model, allowing deployment of the application with customers running a variety of systems.

Rather than replicating data from one system to another, developers can use a consistent data model on top of which to build applications without regard to underlying base system(s) used. Updates/upgrades can thereby be facilitated without downtime and with negligible service cost.

Using existing base tables (e.g., domain tables, etc.) messy synchronization, ETL, data duplication, etc., can be avoided. A database agnostic approach can be provided on multiple platforms while allowing users to retain their current data, for example. Using a single schema that holds information of both the RIS and the PACS, for both and single middle tier, a back end infrastructure can be fused together. Even while the back end infrastructure may be fused together, a client side can retain two applications (e.g., one for exam ordering and one for exam viewing), although a single, combined application can be provided instead. In certain examples, a combination results in a customer paying only one license fee.

In certain examples, the integrated, single schema system includes a scalable image service manager (ISM) that can integrate with a plurality of applications to accommodate scaling of such applications to accommodate and work with a variety of other applications. An imaging connection manager (ICM) provides a level of abstraction between components such that components can plug-and-play by communicating with the ICM, which identifies and understands the component and, in turn, communicates with the ISM, which remains stable throughout. Thus, for example, the ICM can retrieve a study from the ISM based on a study identifier (ID). At the ISM, such interaction to identify a study, fetch the study, and provide the study to a viewer can be coded according to a standard application programming interface (API). On the ICM side, the ICM communicates with the ISM and then provides a system-/application-specific connection on the other side (e.g., an EA connector, a PACS connector, etc.) to enable access.

Certain examples provide a front end user interface system with an integrated front end but not necessarily a unified back end (e.g., disparate systems operating according to a single schema). Certain examples help to facilitate image lifecycle management via the single schema-based system in conjunction with an enterprise archive (EA), DICOM source, modality, etc.

Figure 5:
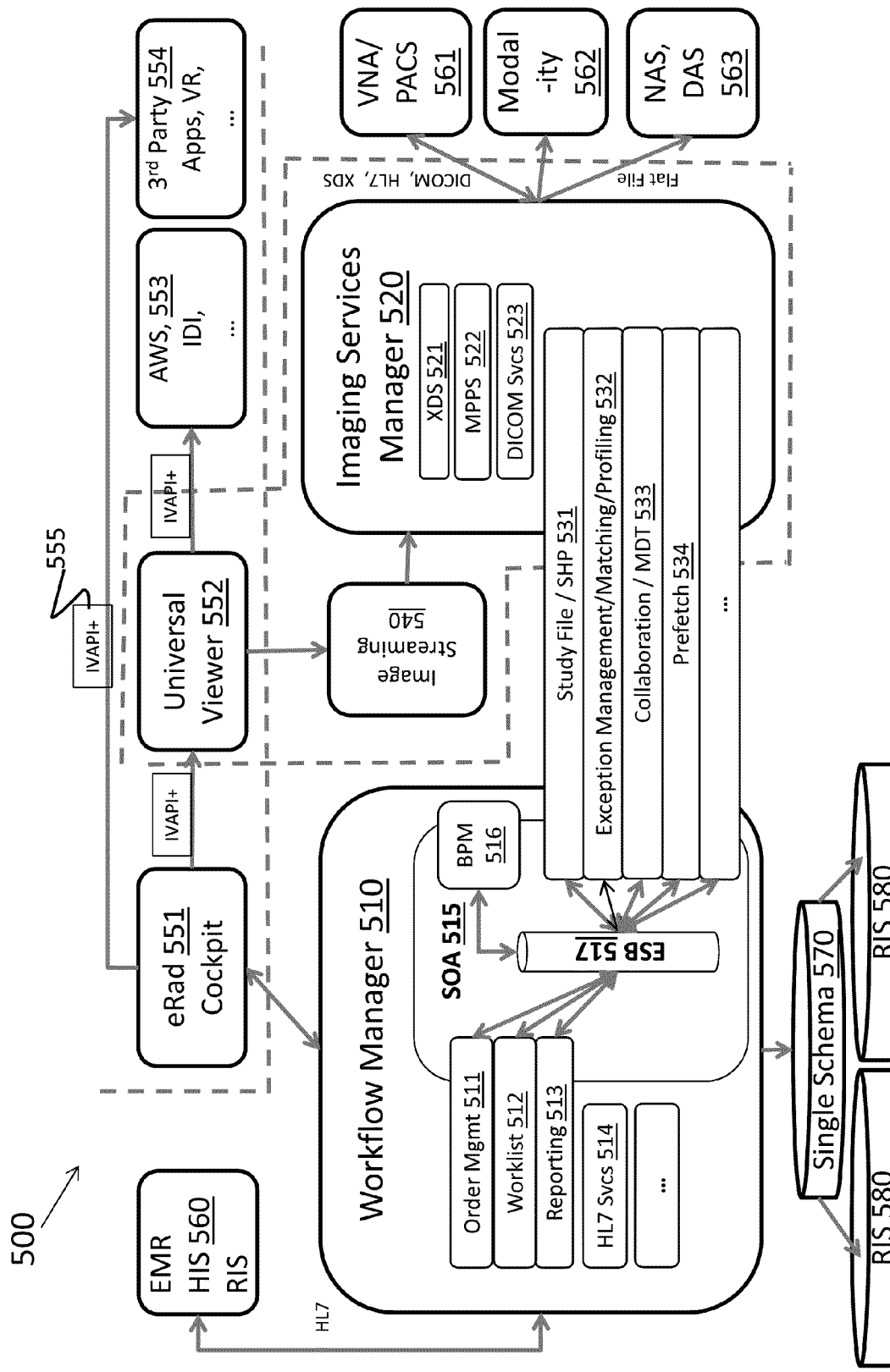
FIG. 5 illustrates an example integrated clinical information system.

FIG. 5 illustrates an example integrated clinical information system 500. The example integrated system 500 includes a workflow manager 510 and an imaging services manager 520 with a plurality of overlapping functionality 531-534.

The workflow manager 510 includes services such as order management 511, worklist 512, reporting 513, messaging (e.g., HL7) services 514, etc. Using an SOA 515, the workflow manager 510 provides BPM 516 and communicates with shared functionality 531-534 via an ESB 517. Via the ESB 517, the workflow manager 510 can shared a study file/SHP 531, exception management/matching/profiling/etc. 532, collaboration/MDT 533, prefetching 534, etc., with the imaging services manager 520. The imaging services manager 520 supports services including XDS 521, MPPS 522, DICOM services 523, etc.

As shown in the example of FIG. 5, a user can access the workflow manager 510 and/or imaging services manager 520 via one or more of a radiology reading and reporting viewer 551 (e.g., a GE Centricity® eRad Cockpit provided by General Electric Company), a universal/zero footprint viewer 552, a modality viewer (e.g., GE Advantage Workstation (AWS), GE IDI Mammography Workstation, etc.) 553, third party application 554, etc. The devices 551-553 can communicate using an application programming interface (API) such as an image viewer API (IVAPI), etc. Orders, worklist, reports, etc., can be accessed via the workflow manager 510 while images can be accessed from the imaging services manager 520. In some examples, an image streaming engine 540 facilitates image location and retrieval from the imaging services manager 520.

For example, a user (e.g., a radiologist) can access his or her radiology review cockpit 551 and launch the universal viewer 552 from the cockpit 551. The universal viewer can communicate with one or more modality image viewers such as AWS, IDI, etc., 553. Using the universal viewer 552, the user can request an image study from the imaging services 520 via the image streaming engine 540. The imaging services 520 works with the workflow manager 510 via the shared functionality 531-534 to retrieve and display the requested image study for the user via the viewer 552. Via the cockpit 551, the user can also retrieve a worklist, associated orders, etc., and generate a report after reading the study images via the workflow manager 510. Reports and/or associated orders can be retrieved and/or stored at one or more RIS databases 580, 581 according to a single, common schema 570.

Additionally, the workflow manager 510 can interact with one or more information systems 560, such as an electronic medical record (EMR), electronic health record (EHR), hospital information system (HIS), RIS, etc. The imaging services manager 520 can similarly communicate with one or more systems including a PACS, EA, and/or VNA 561, an imaging modality (e.g., x-ray, computed tomography (CT), mammography, magnetic resonance imaging (MRI), ultrasound, position emission tomography (PET) scanner, etc.) 562, data storage (e.g., network-attached storage (NAS), direct-attached storage (DAS), etc.) 563, etc.

Thus, in certain examples, the integrated system 500 serves as a fully functional RIS with a built-in image viewer. In such examples, while the example system 500 does not perform image acquisition and archiving, the system 500 communicates with an EA and/or other image storage for archiving, acquisition, etc. The imaging services manager 520 provides smart hanging protocols, user privileges, resources, etc., along with images for the universal viewer 552 to function.

In certain examples, an imaging connection manager (ICM) is provided between the imaging services manager 520 and the one or more imaging back-ends 561-563. ICM connector modules are written for various back-end systems including EA, PCAS, DICOM, XDSi, third party imaging backends, etc., so that intricacies of such connections are abstracted from the rest of the system 500.

In certain examples, image metadata and location can be directly extracted from an EA and/or other image store database. The streaming engine 540 can pull images off of the EA cache for display. In certain examples, the system 500 queries/polls the EA and/or other archive for arrival of new studies or changes to existing studies. HL7 messages can be sent back to the EA/other image store for patient demographic update, for example.

In certain examples, native prefetching can be provided to populate an image cache for first image display (e.g., in less than two seconds). In other examples, a temporary file space can be provided with the system 500 to provide transient storage such that images are stored as temporary files for a fraction of the time it would otherwise take to receive them from a remote DICOM service and pass them to the universal viewer. In certain examples, a digest or pre-digest is provided to gather or prefetch certain image attributes to determine a first image to be displayed in the system 500 database. A single, expanded schema can be used to keep information (e.g., image attributes and relationships) to speed up first image display time and dynamically query at every request for view, for example.

In certain examples, the single schema encompasses representations from both EA and RIS as well as supporting functionality/data provided by a traditional PACS. Rather than separate RIS and PACS schema that have different formats and are stored and interpreted in different ways, one schema provides one definition of a patient, an order, a visit, etc., that is shared by RIS, PACS, and/or other clinical system. A common schema allows multiple systems to look at a patient according to their various data sets (e.g., PACS data, RIS data, etc.) using the same interpretation (and, for example, with the same middle tier for formatting, analysis, etc.). The variety of data for that patient can then be broken down and analyzed from a RIS perspective, a PACS perspective, an integrated RIS/PACS perspective, a worklist perspective, and/or other configuration of the same code, for example. Using the single schema, a pre-digest of information that would otherwise be pulled at runtime from different sources can be gathered and interpreted up front so that it is available when needed or desired. Using a single schema, functionality can communicate without using a broker as a translator or intermediary, for example.

The schema supports both objects of domain and objects of design. Domain objects can be reconciled into common, updatable views based on tables (e.g., tables based on domain entities such as patient, visit, exam, master file data, etc.). Design objects can often be eliminated from the integrated system due to equivalently functionality already existing in the system. However, design objects without an equivalent can be added without conflict. Tables can be created for non-domain objects and transactional data such as audit, implementation of rules, user preferences, etc. In certain examples, the common schema is based on a RIS schema extended for integrated system features. As such, some RIS design objects may be excluded. Using the common integrated schema, application developers get a consistent, database agnostic, data model on top of which to build applications regardless of an underlying RIS (e.g., in the case of a "bolt-on" embodiment to an existing RIS, etc.), for example.

Figure 6:
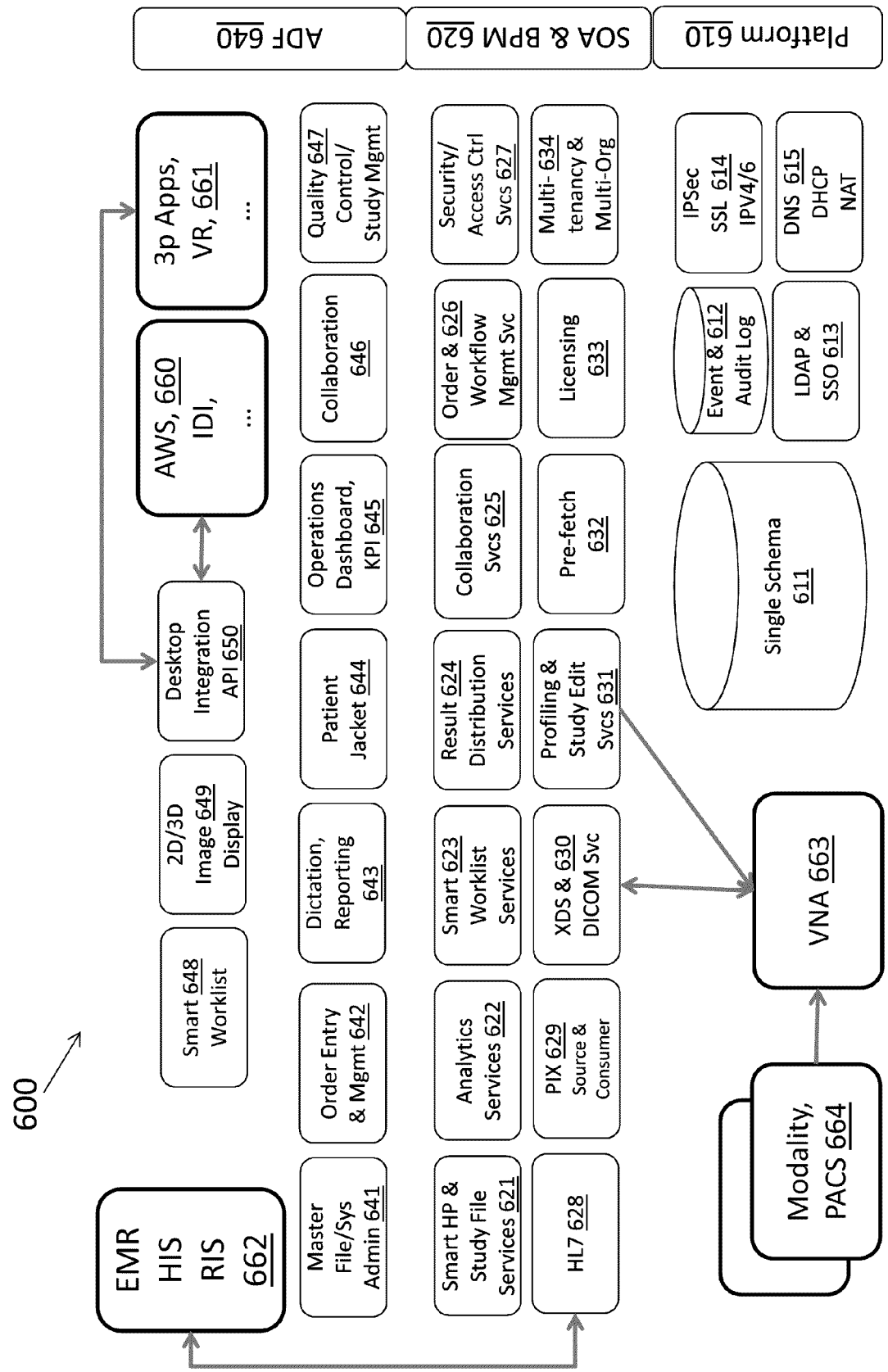
FIG. 6 depicts an architecture diagram for an example integrated clinical system.

FIG. 6 depicts an architecture diagram for an example integrated clinical system 600 (e.g., similar to the system 500 of FIG. 5). The example system 600 is organized according to three tiers/levels/layers: platform 610, SOA and BPM 620, and application development framework (ADF) 640.

The platform 610 includes a single, unified schema 611 used to define, organize and store information (e.g., whether traditionally "RIS data", "PACS data", etc.). The platform 610 also includes an event and audit log 612, access protocol (e.g., lightweight directory access protocol (LDAP), single sign-on (SSO), etc.) 613, communications security (e.g., Internet Protocol Security (IPSec), secure sockets layer (SSL), Internet Protocol version 4 or version 6 (IPV4/6, etc.) 614, Internet Protocol (IP) and/or other networking services (e.g., domain name service (DNS), dynamic host control protocol (DHCP), network address translation (NAT), etc.) 615, etc. The elements of the platform 610 provide a base for the architecture 620 and applications 630 that sit on top of the platform 610 to form the example integrated clinical system 600.

The service-oriented architecture and business process management 620 of the example system 600 include a plurality of services to drive applications and access, for example. For example, the SOA/BPM 620 provides smart hanging protocol and study file loading/display/arrangement services 621 to arrange and display one or more images in a study (along with associated tools, settings, etc.). Additionally, analytics services 622, smart worklist services 623, result distribution services 624, collaboration services 625, order and workflow management services 626, etc., are provided to facilitate processing of an image and associated data, management of exams in a worklist to be read, distributing of reports and/or other results, collaboration and/or other consultation for review, generating of orders, etc. Further, content and functionality can be regulated through security and access control services 627. Hierarchy and relationships can be governed through multi-tenancy and multi-organization services 634. Licensing constraints and rights can also be managed 633. Image(s) and/or other data can be pre-fetched 632.

Profiling and study edit services 631 can also be provided to a user. For example, a VNA 663 can interact with the XDS/DICOM 630 and profile/study edit services 631 when receiving image data from a source 664 such as from a PACS, directly from an imaging modality, etc. In certain examples, an image cache can be provided in the integrated system 600 to communicate with a third party VNA 663 and/or PACS, as well as XDS/DICOM 630, profile/study edit services 631, and prefetch 632 for image retrieval and temporary storage. In certain examples, a VNA 663 serves as the image cache.

Communications and image/information sharing can be facilitated through HL7 messaging services 628, PIX source and consumer services 629, XDS and DICOM services 630, etc. For example, HL7 messaging 728 can be used to transmit data with an external information system 662, such as an EMR, EHR, HIS, RIS, etc.

Using the ADF 640, one or more applications such as a smart worklist 648, image display 649 (e.g., two-dimensional (2D) and/or three-dimensional (3D), etc.), desktop integration API 650, etc., can be provided. In certain examples, external modality systems 660 (e.g., AWS, IDI, etc.) and/or applications (e.g., third-party applications, voice recognition, etc.) 661 can interface with the desktop integration API 650, for example. Applications can also include master file and/or system administration 641, order entry and management 642, dictation/reporting 643, patient jacket (e.g., single patient jacket) 644, operations dashboard/key performance indicators (KPIs) 645, collaboration 646, quality control/study management 647, etc.

Certain examples provide a scalable system 600 to accommodate a variety of healthcare institutions/providers and to help ensure high availability of the system 600 to its users (e.g., always on, zero downtime upgrade, zero data loss, automated failover, data replication (e.g., lossless replication, etc.), disaster recovery, etc.).

Cross-Enterprise Integrated System Design

In certain examples, one or more integrated systems can be provided and/or can communicate across multiple healthcare enterprises. Certain examples provide cross-enterprise or supra-enterprise communication, collaboration, and information sharing to provide access but retain ownership and/or control of data. For example, an entity's workload can be shared across competitors while enabling that entity to retain control of its customer base but still provide access to (but retain control over) relevant records. In some examples, collaboration may be facilitated between different legal entities with different systems, for example. In certain examples, a user from a local system trying to access data and/or functionality from a remote system can be authenticated by the local system and authorized by the remote system.

FIGS. 7-25 illustrate a plurality of example configurations for cross-enterprise communication and collaboration with an integrated clinical system. Various designs can be configured to help satisfy one or more metrics including serviceability (e.g., installability, upgradability, break/fix workflows, etc.), performance (e.g., throughput, latency, high availability, scalability, etc.), security, usability, product development, and marketability, for example.

Certain examples support cross-enterprise informational constructs such as a single global patient jacket across multiple institutions, a global reading worklist for a radiologist, etc., as well as facilitating reporting into a system from which an exam being read originated. Certain examples facilitate cross-enterprise interaction without a common master file across participating enterprises (but with, for example, a master patient index (MPI)) and without data duplication (e.g., a single system of record).

In certain examples, a cross-enterprise arrangement is decentralized to allow participants to allow and/or restrict people, requests, etc., according to one or more "local" rules, procedures, preferences, etc. A user's local system can be responsible for authentication (is this user who he claims to be?), while a target local and/or remote system may be responsible for authorization (does this user have an ability to do X-Y-Z in my system?). In this way, existing enterprise organizations can be leveraged into a cross-enterprise framework without further change.

For example, a trusted enterprise can reach out to a local machine, and its agent can verify that a user from the trusted enterprise has access. For example, this user is from enterprise A, and this user wants to access certain images from a machine in enterprise C. Enterprise A authenticates the user, and enterprise C authorizes the access (access control is in the hands of enterprise C). Thus, certain examples facilitate authentication of a user at the remote "home" system for the user, but authorize access for the user locally at the system in question. By allowing each user's system to handle authentication and each data/application's system to handle authorization for access to its application/data, certain examples allow for multi-technology users (e.g., different and competing technology stacks can be used together) and cross-application communication.

Further, certain examples facilitate easy transitions for enterprises coming into or going out of cross-enterprise sharing. For example, a user in enterprise A does not need to know anything about users in enterprise C. Enterprise A can set its own rules about users and can revoke and/or change rules, users, etc., at any time without interference from another enterprise. If enterprise C leaves the collaboration, then enterprise C can shut down the external trust previously given to enterprise A and other collaborating enterprises so that enterprise C then treats those enterprises as if it does not know them.

Certain examples help reduce implementation time and complexity (e.g., an implementation time of zero) by leveraging existing infrastructure and/or capability (e.g., LDAP authentication mechanism already built in to local enterprise) versus a centralized authentication/authorization approach (which requires enterprises to maintain their list of users both locally and with respect to the central server). With a centralized approach, if a user is disabled locally but not centrally, that user still has access as far as the central authority is concerned; with decentralized collaboration, the user has to ask the local enterprise.

In certain examples, radiology tasks can be organized in a single, intelligent workflow to collaboratively deliver more efficient patient care and improved utilization of imaging resources. Certain examples facilitate automatic prioritization of studies across an enterprise based on a radiologist worklist, based on the skill, sub-specialty, experience and service level agreements, and so on. Certain examples help to enhance virtual collaboration between radiologists, referring physicians, and other specialists to improve confidence in diagnostic findings. Certain examples enable distributed radiologists to share reading workload for studies performed at other locations. Certain examples provide a workflow-enabled, comprehensive solution to image management, reporting, and analytics to help drive patient care. Certain examples provide native tag morphing to optimize or otherwise improve image sharing and workflows via a diagnostic viewer. Certain examples facilitate enterprise and community wide collaboration (e.g., via a cloud-based and/or other server-based infrastructure, etc.).

Figure 7:
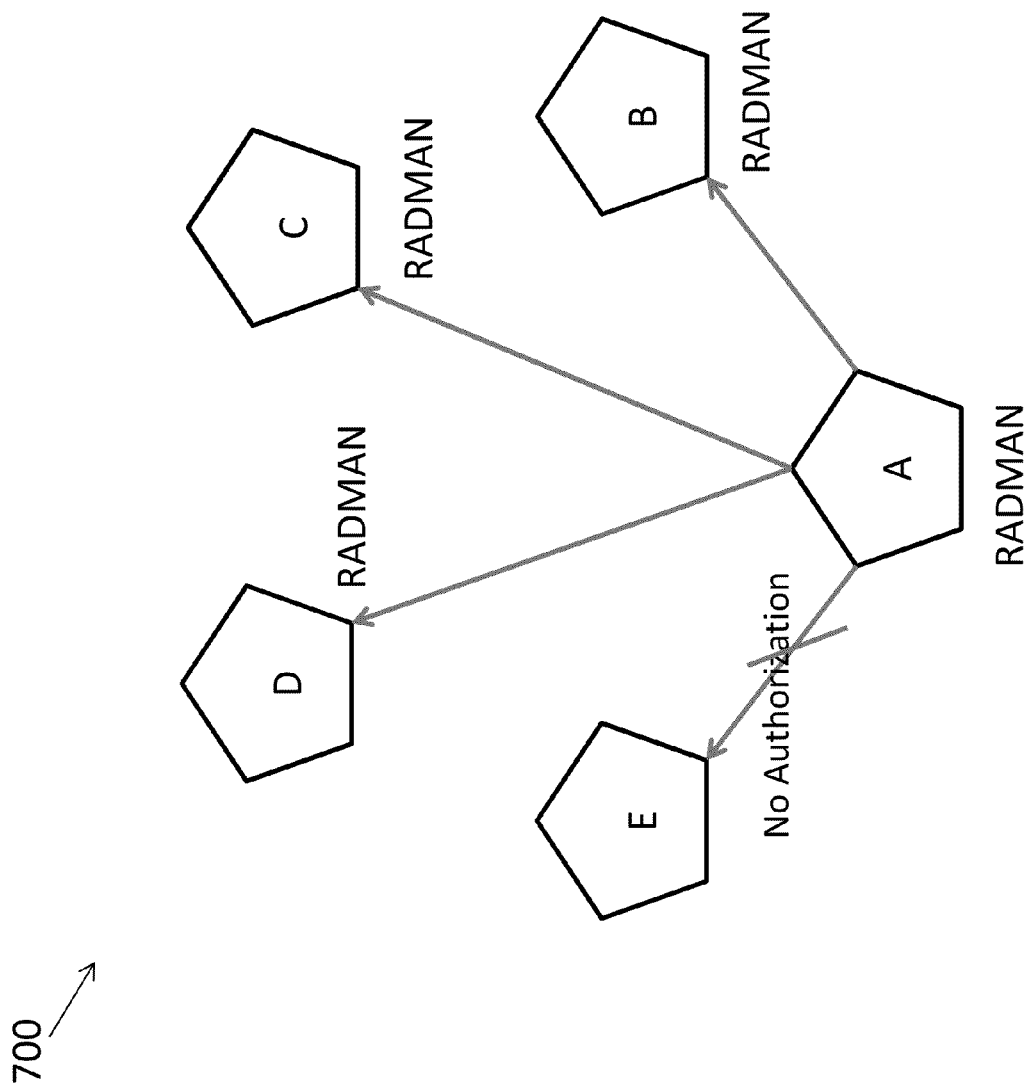
FIGS. 7-19 illustrate a plurality of example configurations for cross-enterprise communication and collaboration with an integrated clinical system.

FIG. 7 illustrates an example (simplified) cross-enterprise authentication and authorization configuration 700. As depicted in the example of FIG. 7, user accounts are created in each enterprise that allows a radiologist to view a cross-enterprise patient jacket. Passwords are kept in synch using an external mechanism. A database (e.g., Oracle® database) link is used to connect an enterprise to one or more remote databases. Only barebones authorization is provided (e.g., none or all) in the example configuration of FIG. 7.

Figure 8:
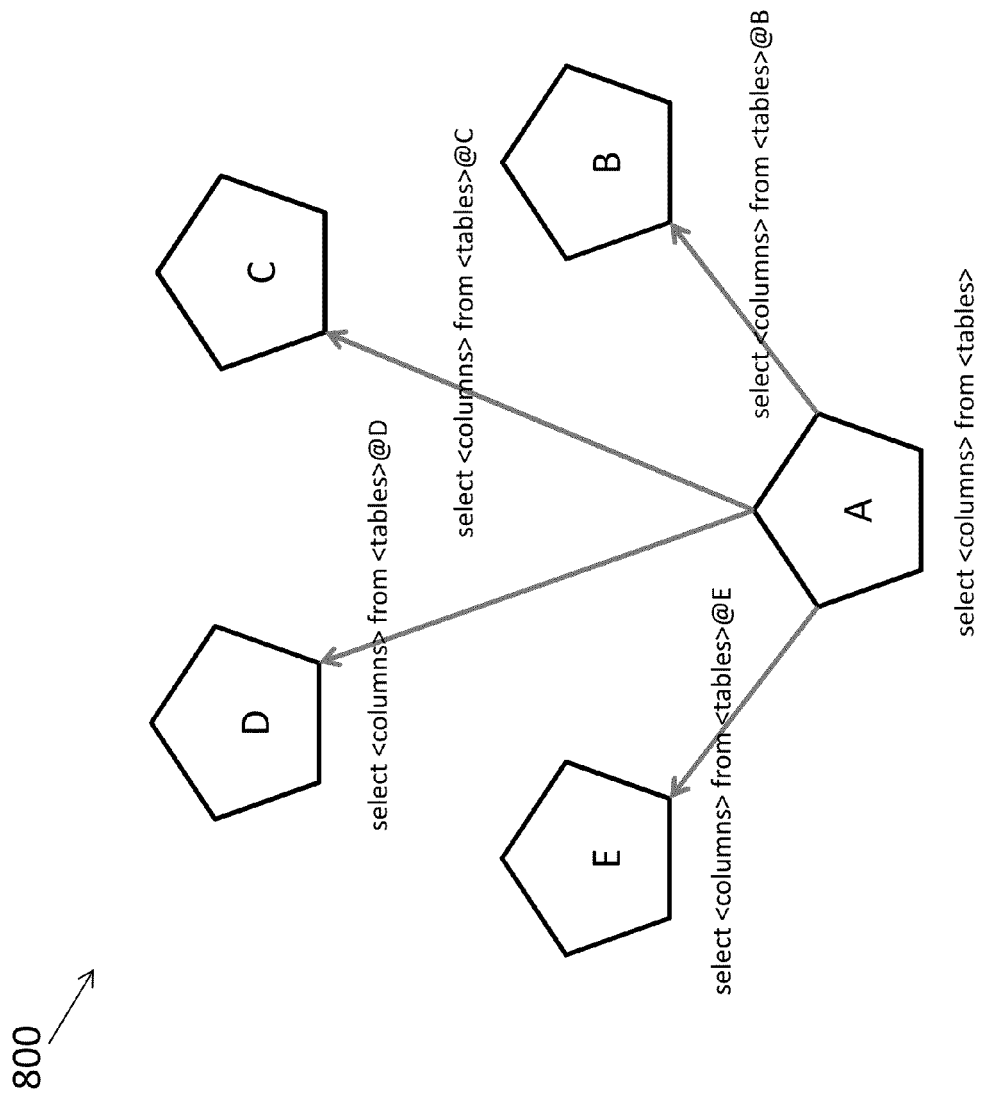

FIG. 8 illustrates an example sharing of a global worklist and patient jacket based on the cross-enterprise design 700 of FIG. 7. As demonstrated in the example configuration 800, database (e.g., SQL) query results from local and remote sources are aggregated to be presented as a single patient jacket. Application development (ADF)/business component (BC) is tied to a stored procedure that returns the patient jacket when called. The single patient jacket uses temporary tables, procedural language/structured query language (PL/SQL) tables, etc., and handles exceptions internally. Master file data (MFD) indicating exam source can be provided for remote exams, which each include a reference to its local enterprise. As shown in FIG. 8, enterprise A selects columns from its patient data tables and selects columns at enterprises B, C, D, and E that relate to the patient as well for inclusion into a single patient jacket.

Figure 9:
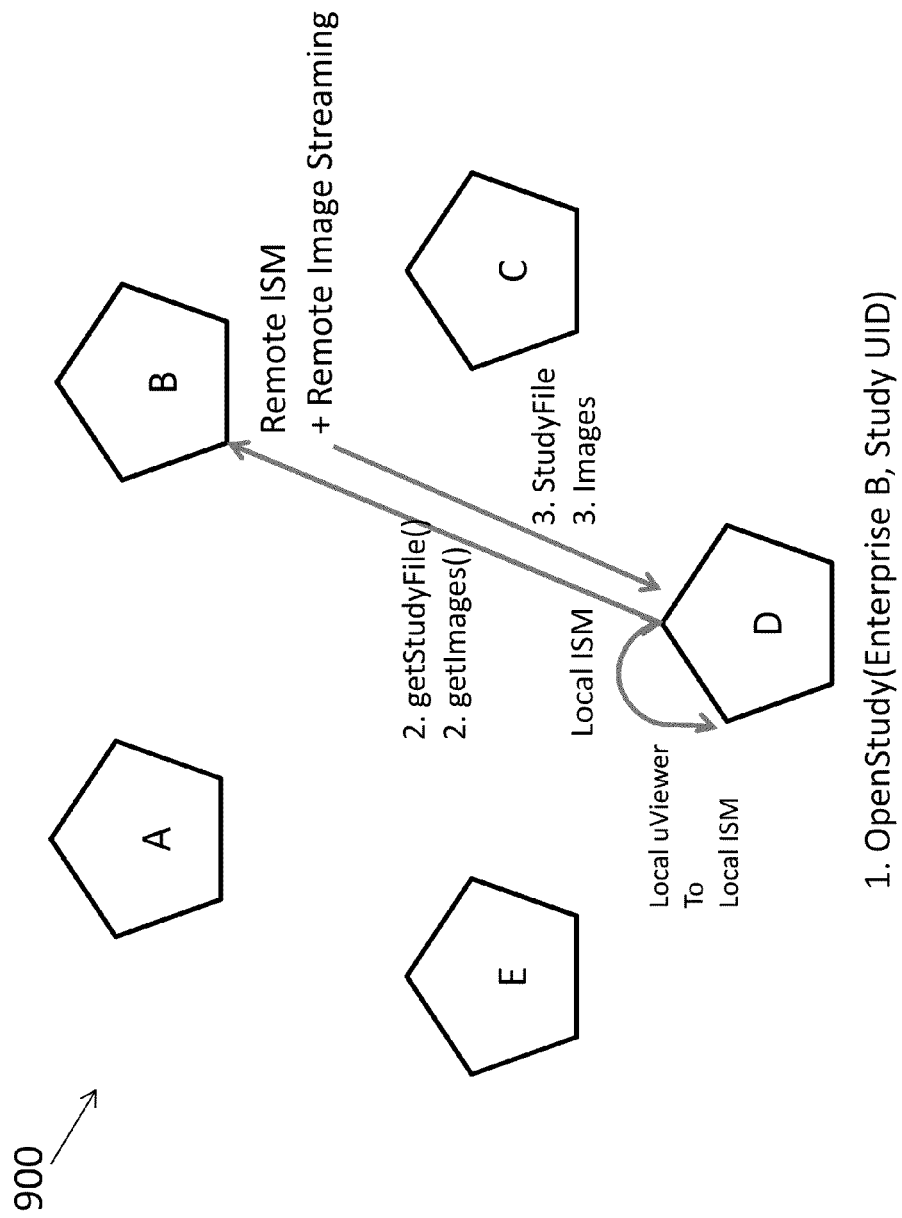

FIG. 9 illustrates an example opening of a study residing on enterprise B via a viewer in enterprise D based on the cross-enterprise design 700 of FIG. 7. A user in enterprise B opens a study (e.g., via a universal viewer launched from a radiology workspace/cockpit) based on a study identifier (e.g., a unique identifier (UID), enterprise code for the study, etc.). The study is found at remote system B. Thus, the universal viewer of enterprise D sends a request for the study file and associated image(s) to a local ISM at enterprise B. The local enterprise D authenticates the requesting user, and the remote enterprise B verifies authorization of the requesting user at enterprise D to access the identified study at enterprise B. The remote enterprise B locates and streams the exam using, for example, an image streaming engine, and transfers the study file and image(s) for display via the viewer at enterprise D. The study file can be added to a worklist of the requesting user at enterprise D, for example. The worklist can indicate that the exam is a cross-enterprise exam (and being provided remotely), for example. Display characteristics and order information from remote system B can be used for display of the image(s), and display settings such as grayscale softcopy presentation state (GSPS) information for the image(s) can be saved at the remote system B, for example.

Figure 10:
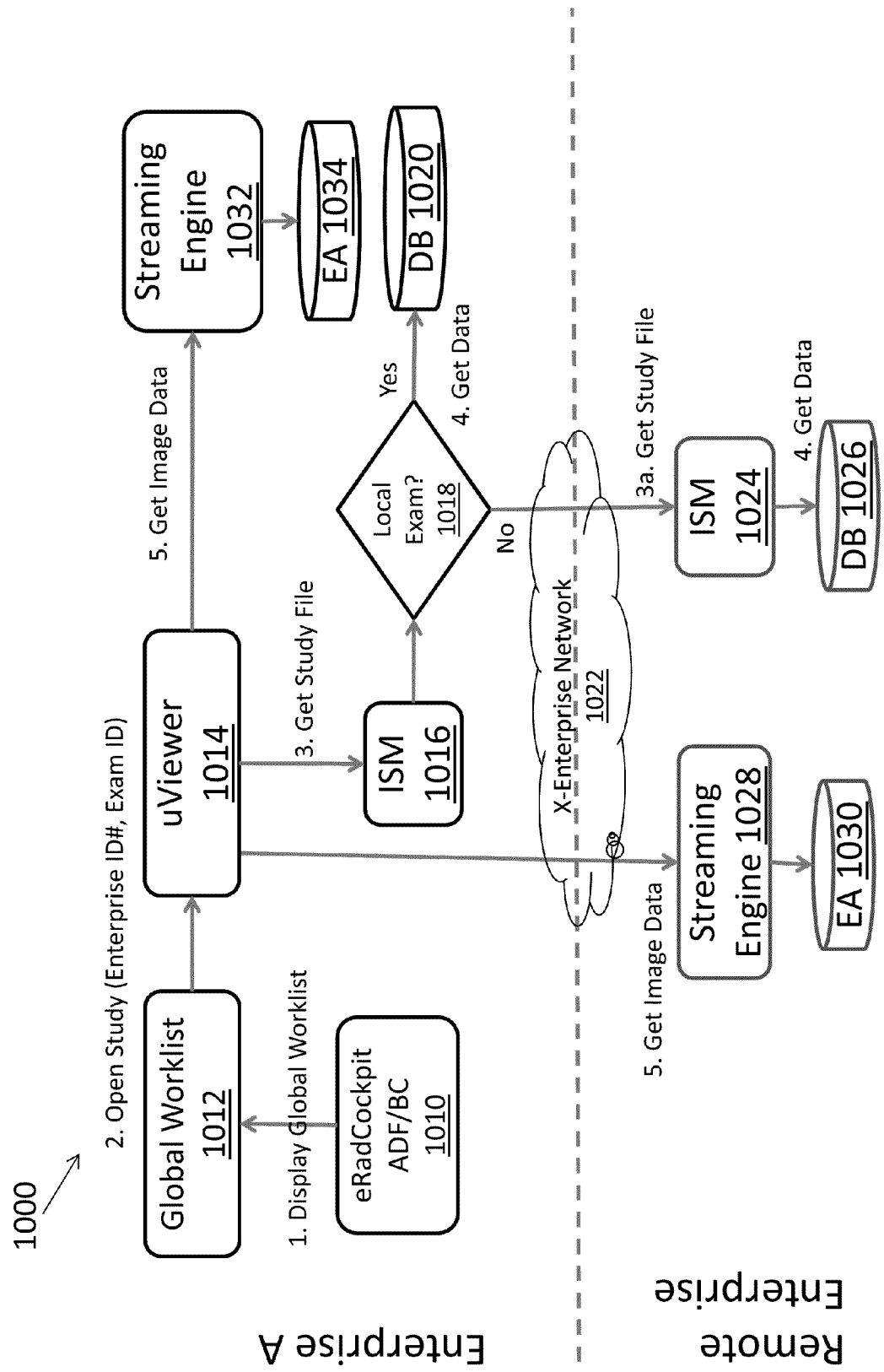

FIG. 10 provides an alternate view of an example cross-enterprise open study sequence 1000 between a local enterprise A and a remote enterprise storing the image study. As shown in the example of FIG. 10, a user at a radiology reading workstation 1010 displays a global worklist 1012 and selects a study from the global worklist 1012 based on enterprise identifier and exam identifier, for example. A universal viewer 1014 retrieves the requested study file from an ISM 1016, which determines, at 1018, whether the requested exam is local to enterprise A or not. If the exam is local, then the ISM 1016 gets the study data from a database 1020. If the exam is not local, then the ISM 1016 utilizes a cross-enterprise network 1022 to get the study file from an ISM 1024 at the remote enterprise holding the data. The remote ISM 1024 gets the study file data from a database 1026 at the remote enterprise, for example.

Alternatively or in addition, the viewer 1014 can get image data from one or more image streaming engines 1028, 1032. A first image streaming engine 1028 is located at the remote enterprise, with access to retrieve the requested image data from an EA 1030. A second image streaming engine 1032 is located at local enterprise A, with access to retrieve the image data from an EA 1034.

Figure 11:
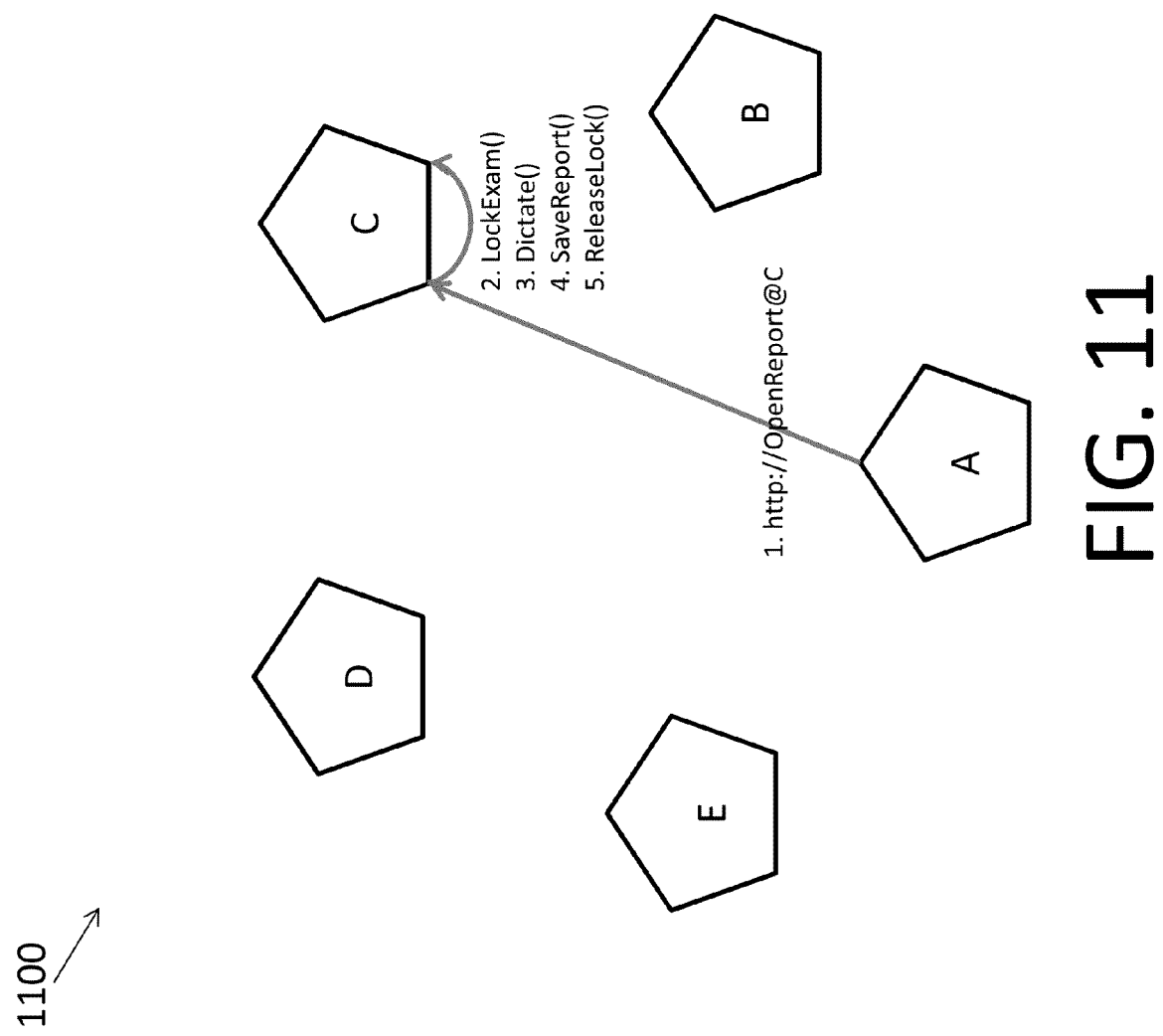

FIG. 11 provides an example configuration 1100 for remote reading of a remote exam based on the cross-enterprise design 700 of FIG. 7. For example, a user seeks to dictate a report of an exam stored remotely at system C based on voice recognition (VR). The use opens a remote report (at system C) via a local system (system A). In response, the exam is locked at remote system C. While a local VR system is used at system A, a report generated is stored at the remote system C. An order does not exist in the local system A but, rather, is found in remote system C. No remote order artifacts are created in the local system A.

In certain examples, a directory service, such as Microsoft™ Active Directory, for user authentication and authorization can be added to cross-enterprise configurations to provide better control by individual enterprises over their data and its access. The directory service or SSO access control can be used to authenticate between enterprises without password exchange, resulting in better security. Web services, which enable multi-threaded processing at lower latency than direct SQL, can be used instead of direct SQL, for example, to create a reading worklist, patient jacket, etc. Remote web services can be used to get data instead of directly opening remote portlets within an ADF. Data can be collected from remote systems by a local system and presented from the local system. Cache optimizations can improve data retrieval, lower latency, and reduce network interruptions, for example.

Figure 12:
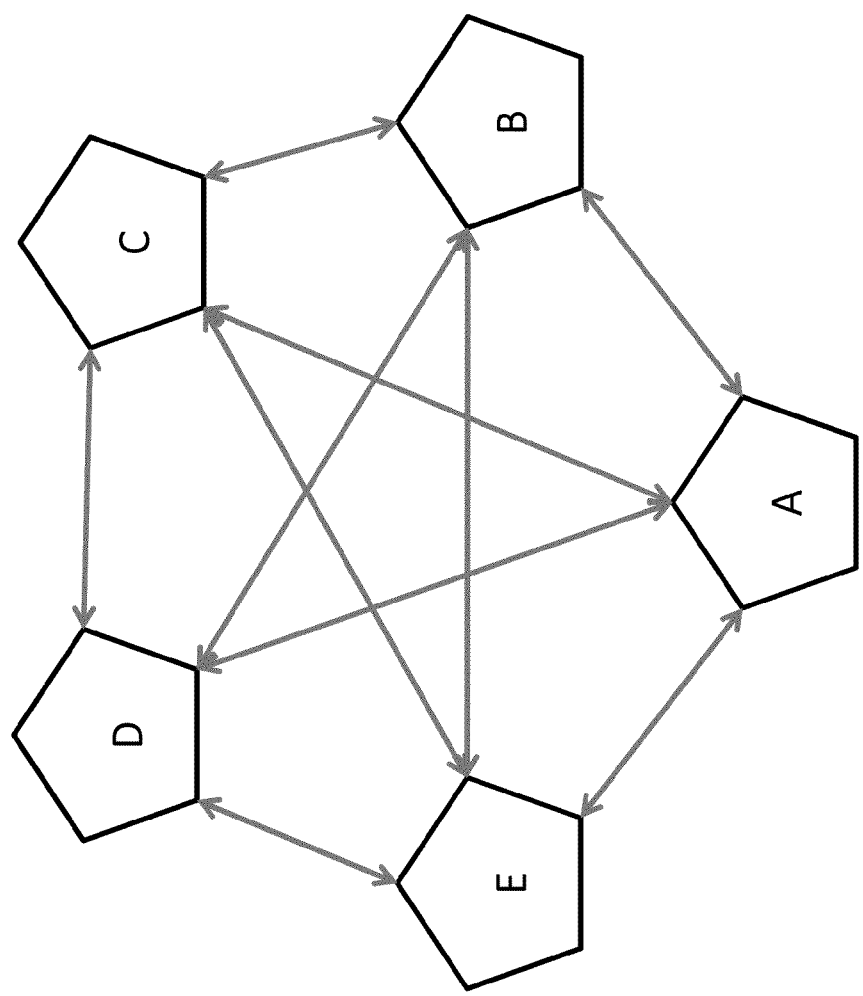

FIG. 12 depicts an example cross-enterprise configuration 1200 using active directory services for authentication and authorization. The configuration 1200 of FIG. 12 provides totally decentralized authentication and authorization. SSO can be used with directory services to provide tightly integrated authentication and authorization. Radiology domains within each enterprise forest can provide access through two-way external trust, for example. Each participating enterprise A-E chooses to which cross-enterprise user access is granted, as well as an associated level of access. Participating enterprises retain full access control to their own systems. Directory services can authenticate and authorize referrals as well without user management. Users can be provisioned and managed by information technology (IT) staff at an enterprise rather than radiology admin, for example.

Figure 13:
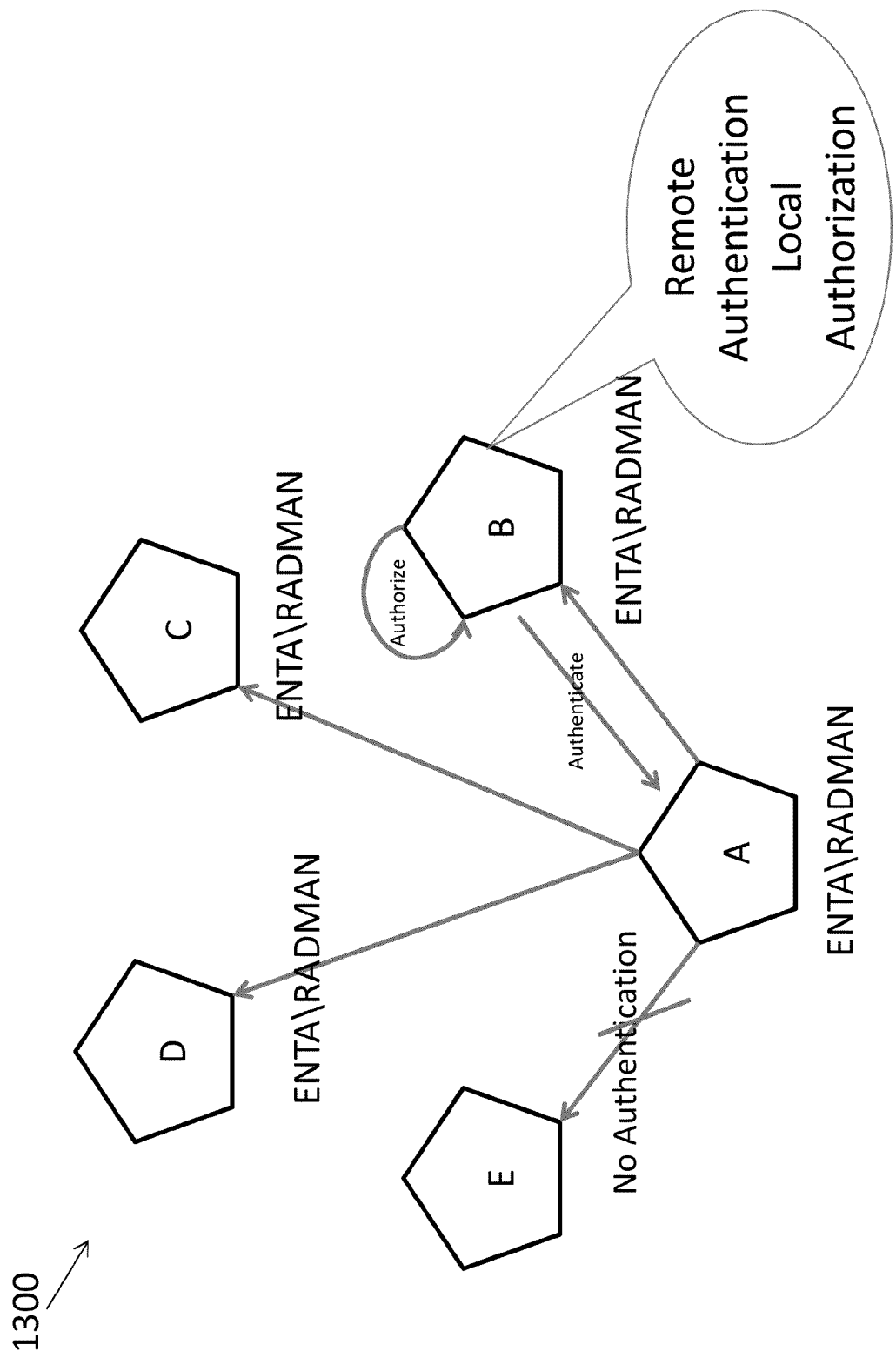

FIG. 13 illustrates an example cross-enterprise configuration 1300 for authentication and authorization using active directory services based on the cross-enterprise design 1200 of FIG. 12. As shown in FIG. 13, remote user accounts are given local group privileges to allow access to local data at remote enterprises in the cross-enterprise configure 1300. Local group privileges can be used to provide SSO-enabled access to resources such as Web services, ISM, image streaming engine, zero footprint viewer, etc. As shown in FIG. 13, a radiologist at enterprise A may be remotely authenticated at enterprise B and then authorized locally at enterprise A. Some enterprises, such as enterprise E, may not provide authorization to remote enterprise A.

Figure 14:
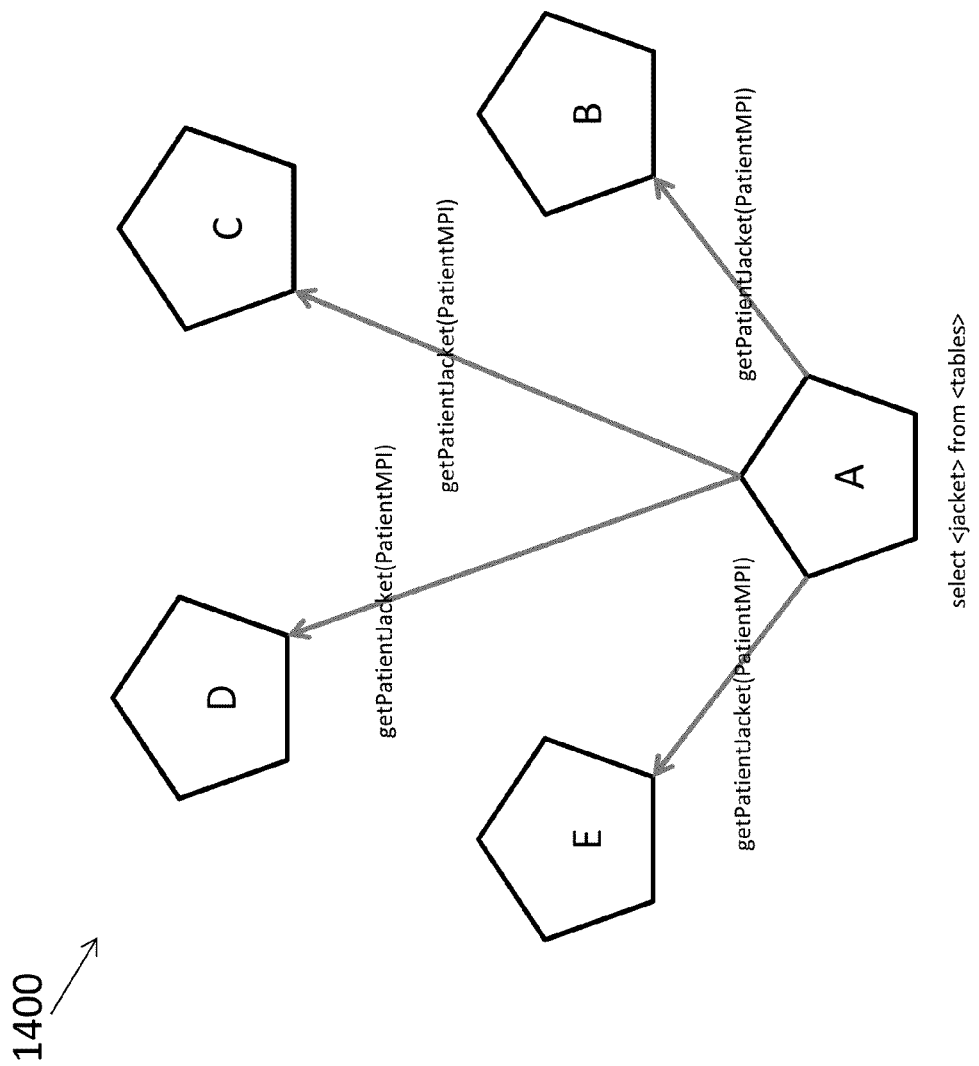

FIG. 14 illustrates an example cross-enterprise configuration 1400 for a single patient jacket based on the network design 1200 of FIG. 12. Using the configuration 1400, web service queries can be aggregated from local and remote sources to be presented as a single patient jacket. Remote master file data (MFD) can be provide for remote exams. Each exam includes a reference to its enterprise (e.g., A, B, C, D, E).

In certain examples, an exam object includes information such as patient name, patient identifier(s), visit identifier, date(s), etc. These are transactional elements largely unique to the exam. In addition, MFD is attached to the exam such as in which facility and department the exam was performed, a name of a procedure performed (CT CHEST), attending physician, dictating physician, etc.

MFD represents a minimum set of data that defines a healthcare enterprise including its enterprise structure such as names of facilities, departments, locations, etc., found in the enterprise; names of procedures performed; and users and their groups, for example. However, remote MFD is not applicable to the local site. Yet, in certain examples, a remote exam includes MFD information as part of its definition. In certain examples, MFD can be duplicated in a local system. Alternatively or in addition, reporting on a report exam in the remote system eliminates a need to duplicate MFD in the local system. Instead, the application bypasses the local system and fetches data from and updates the remote system directly, for example.

Figure 15:
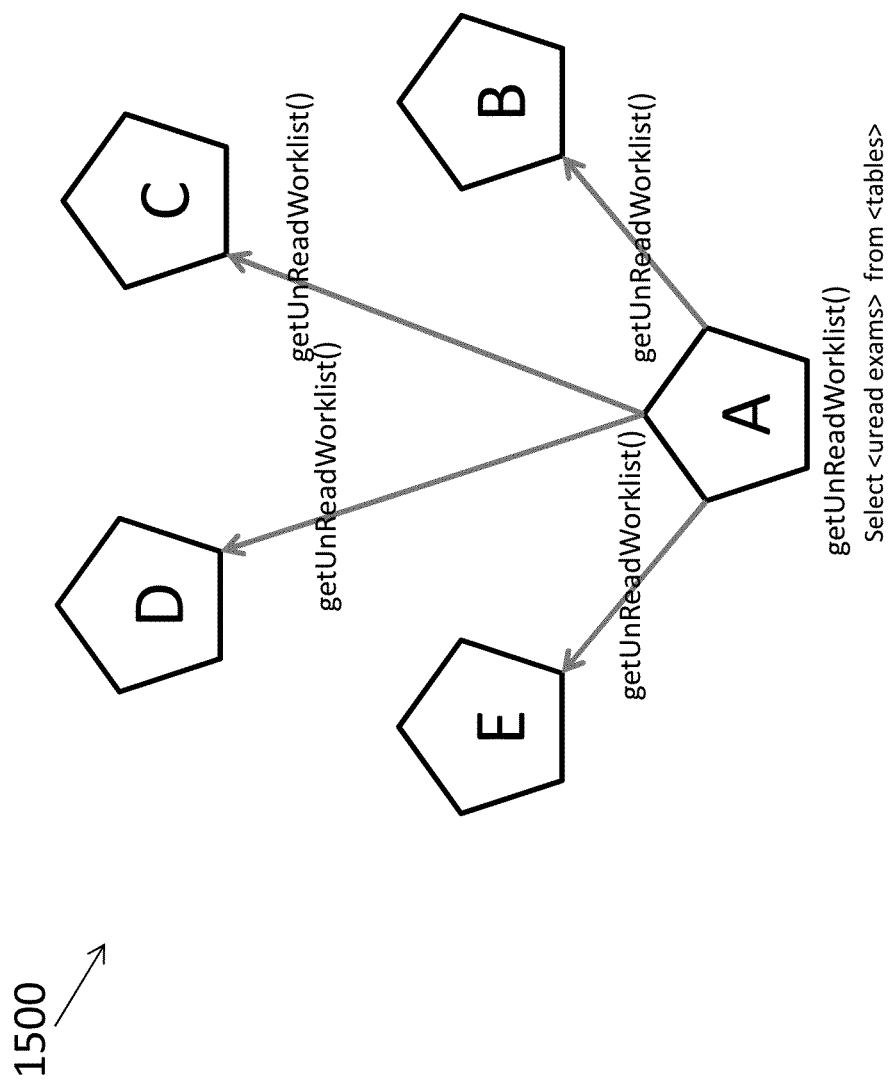

FIG. 15 depicts an example cross-enterprise system configuration 1500 providing a global reading worklist using a radiology reading cockpit based on the cross-enterprise design 1200 of FIG. 12. The example configuration 1500 can be implemented similar to the patient jacket configuration 1400. In the example of FIG. 15, a user's radiology reading cockpit in enterprise A creates a global reading worklist of unread exams. By querying participating enterprises B, C, D, and E, a set of unread exams can be gathered cross-enterprise into a single list for user review and further action.

In certain examples, additional privileges and/or filters can be introduced (confidential patient, anonymization, etc.) in a service layer. Privileges can be rule-based (e.g., time of day, modality type, specialty, etc.), for example, and can be tied into the unread exams list that is returned to the requesting user. Filters can be controlled by the particular enterprise that owns the order for the global reading list, for example. In certain examples, a radiology workstation can pull data from remote systems for remote exams using Web services for display via the local radiology workstation.

Figure 16:
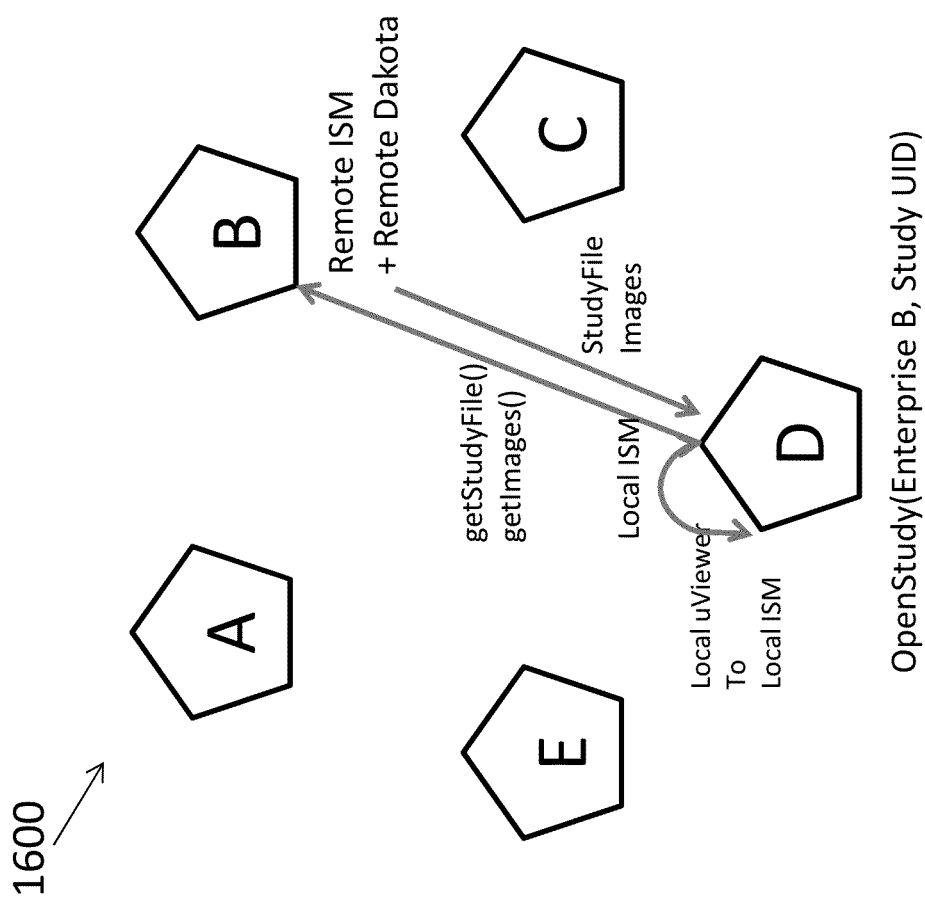

FIG. 16 shows an example cross-enterprise configuration 1600 to open a study file for radiology review based on the design 1200 of FIG. 12. As depicted in the example of FIG. 16, a radiology reading application launches a viewer based on an enterprise code of a desired study for review. A local ISM (at enterprise D) accesses the study file from a remote ISM (at enterprise B) on behalf of local viewer (at enterprise D). A remote streaming engine at the remote enterprise (enterprise B) can be used to transfer image(s) in the requested study to the reader at enterprise D. The study can be listed in the requesting user's worklist (potentially with an indicator indicating the study is a cross-enterprise referenced exam). GSPS and/or other display information can be saved in the remote system (enterprise B), for example.

Figure 17:
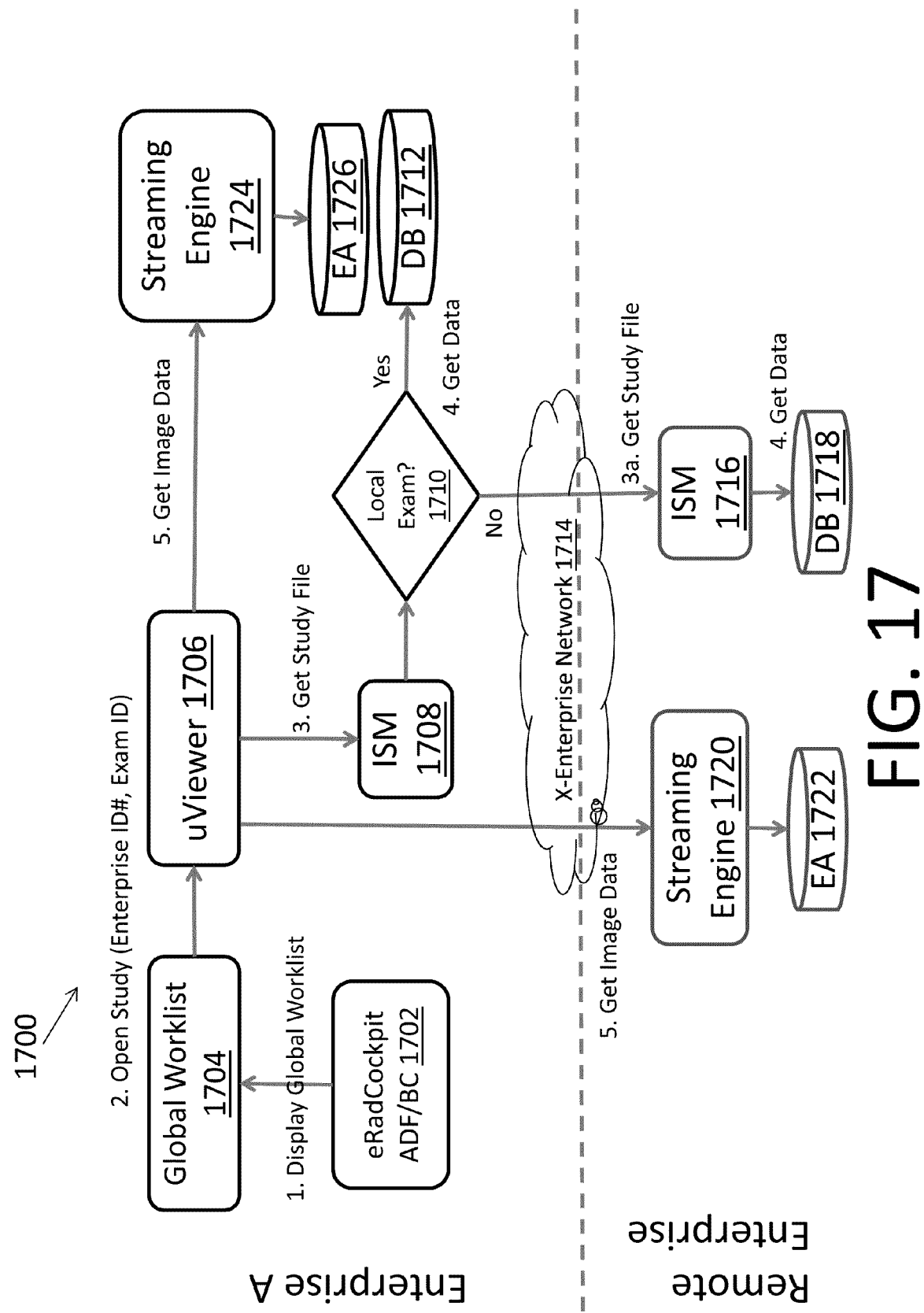

FIG. 17 provides an example cross-enterprise open study sequence 1700 based on the cross-enterprise design 1200 of FIG. 12. As shown in the example of FIG. 17, an application development framework of the radiologist cockpit 1702 requests display of a global worklist 1704. The global worklist 1704 includes a plurality of studies for review. A particular study can be selected from the worklist 1704 to be opened based on an enterprise identifier and exam identifier. The study identification is sent to a viewer 1706, which retrieves the study file via an ISM 1708 at local enterprise A. The ISM 1708 determines whether an exam associated with the study file is local or remote. If the exam is local, then the study file data is retrieved from a local database 1712. If the exam is not local, then the ISM 1708 communicates via a cross-enterprise network 1714 with a remote ISM 1716 at a remote enterprise. The remote ISM 1716 can get the study file data from a database 1718. Alternatively or in addition, the viewer 1706 can get image data from a local image streaming engine 1724 and/or from a remote image streaming engine 1720. The streaming engine 1720, 1724 retrieves the image data from an associated EA 1722, 1726.

Figure 18:
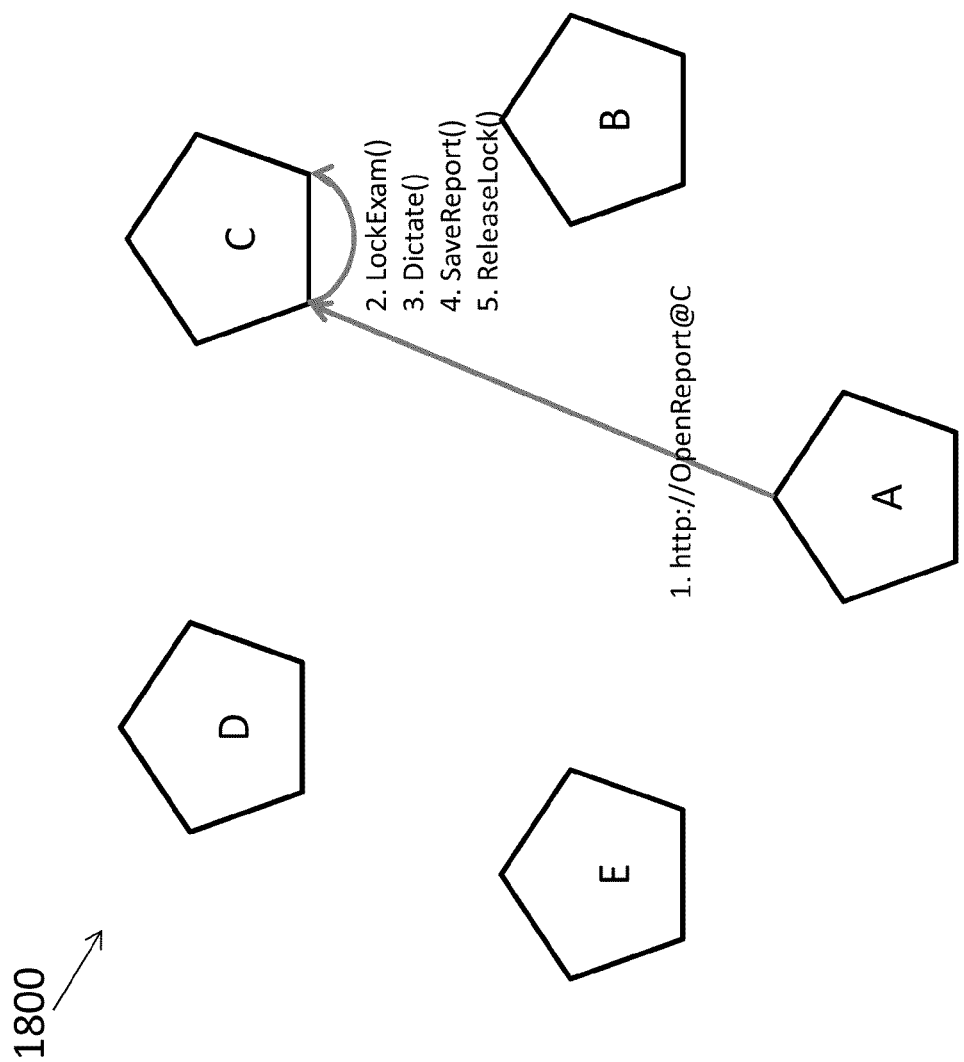

FIG. 18 illustrates an example cross-enterprise system configuration 1800 to support remote radiology reading for a remote exam based on the cross-enterprise design 1200 of FIG. 12. A local user in enterprise A wishes to dictate (e.g., via voice recognition) an output of reading an exam stored in a remote enterprise (enterprise C). The requested exam is locked at the remote system C. A local VR system is used, but a resulting radiology reading report is generated and stored in the remote system. The order does not exist in the local system, and no remote order artifacts are created in the local system.

Figure 19:
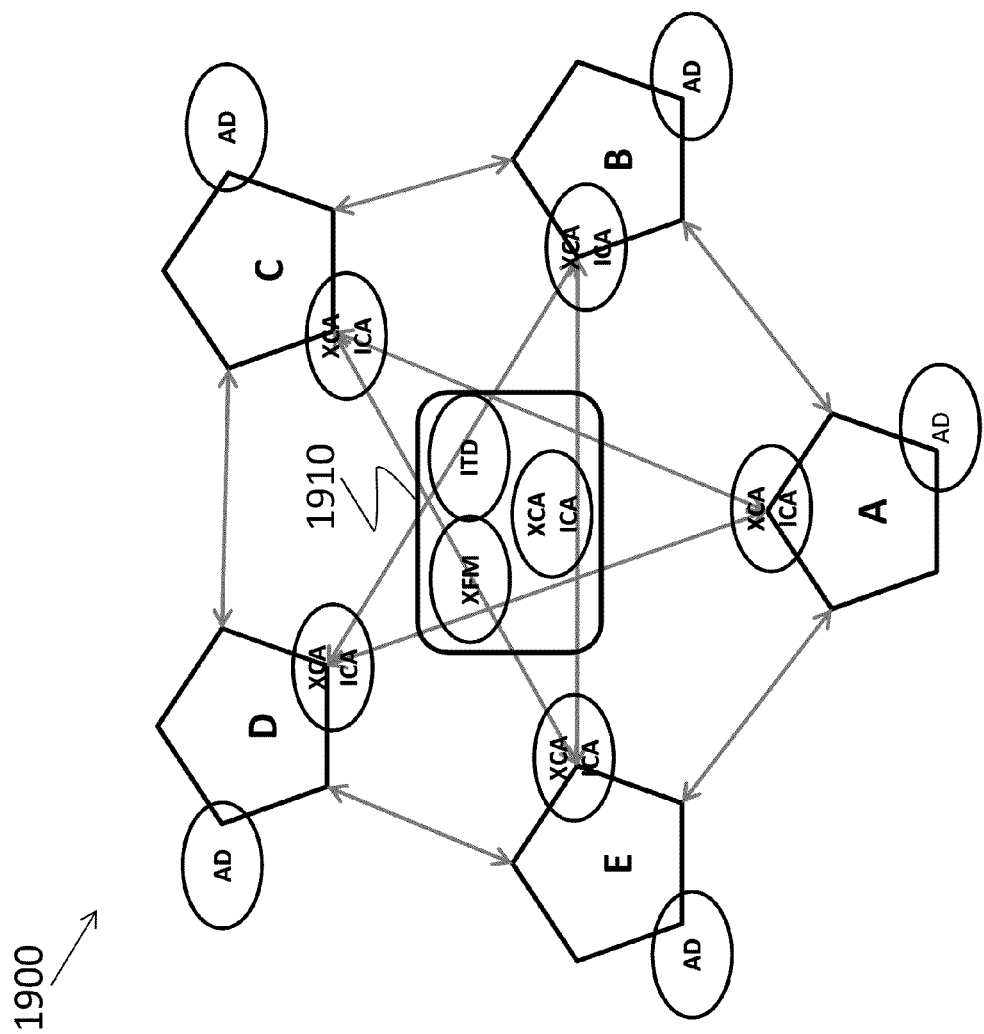

In certain examples, an alternative design uses a central "orchestrator" including automated configuration of a grid of cross-enterprise entities according to a cross-enterprise fabric manager (XFM). Worklist/jacket data can be cached using a coherence-based cross-enterprise caching appliance (XCA) in addition to an imaging cache appliance (ICA) for pre-fetch. An imaging traffic director (ITD) can be used to route to a fastest path to images (e.g., remote system, backup data center, XCA, etc. Certain examples provide high availability, scalability, fault tolerance, application service provider model, remote archive, enhanced serviceability, etc. As shown in FIG. 19, an example cross-enterprise grid configuration 1900 retains a de-centralized, locally access-controlled data environment but adds a "federal" oversight and/or control. The example grid configuration 1900 provides federal control via an XFM, ITD, XCA, and ICA at a centralized node 1910, while each individual enterprise node A-E retains its own XCA, ICA, and active directory services.

In certain examples, cross-enterprise data use and data access can be separated by a "shim" layer designed to help ensure compatibility between systems, applications, etc. For example, a shim can be implemented as a library that transparently intercepts an API and changes parameters passed, handles operations, and/or redirects operations to help ensure compatibility between different systems, platforms, versions, etc.

Figure 20:
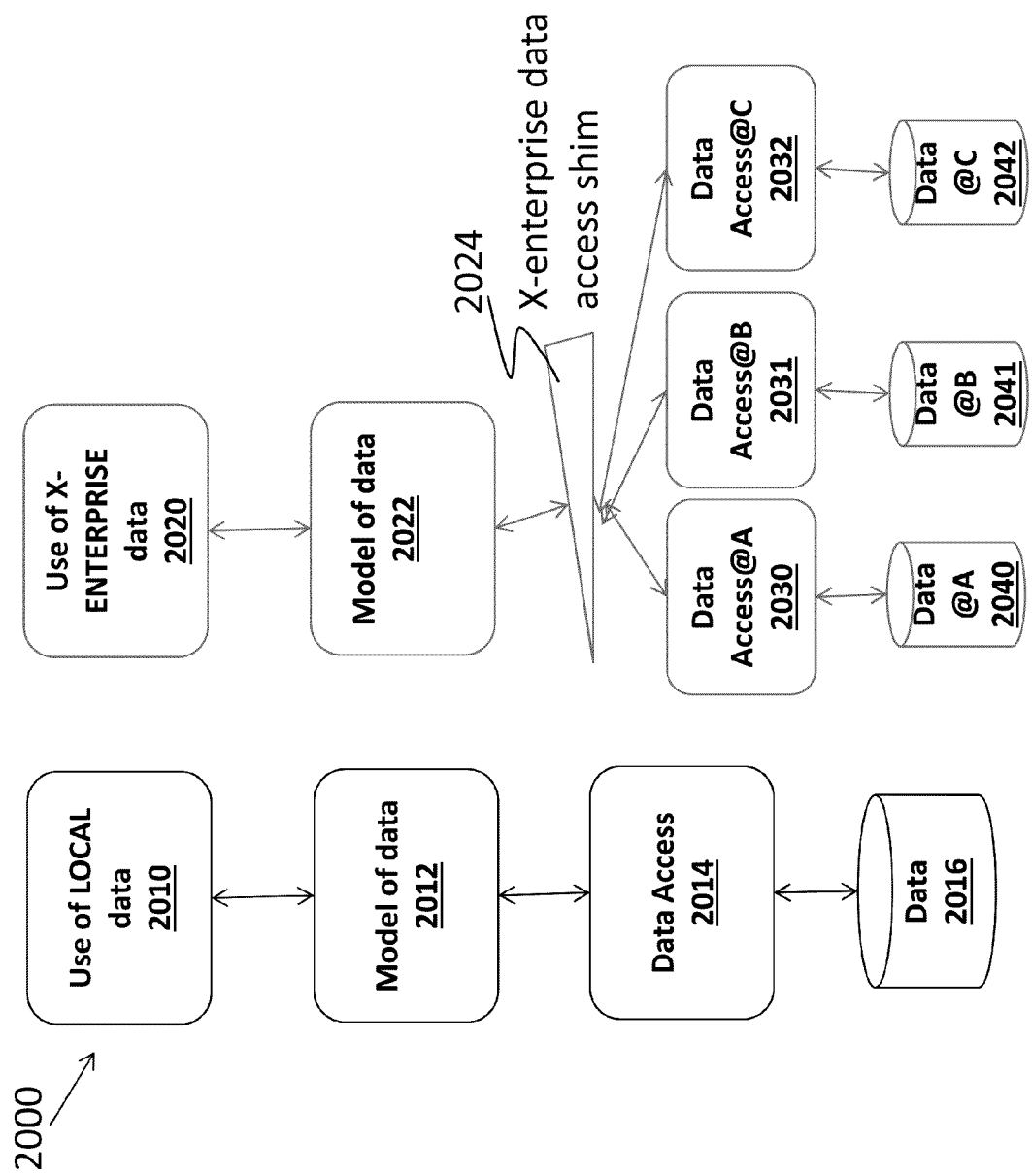
FIG. 20 illustrates an example cross-enterprise data flow diagram showing examples of local data access versions cross-enterprise data access.

FIG. 20 illustrates an example cross-enterprise data flow diagram 2000 showing examples of local data access versions cross-enterprise data access. Using local data 2010, a data model 2012 and data access 2014 are known and can be governed by a local enterprise controlling the data 2016. However, when using cross-enterprise data 2020 (e.g., retrieving data from a remote enterprise to be used at a local enterprise), a model of data 2022 is provided from a requesting system (e.g., exam data tagged with an enterprise code) and received by a cross-enterprise data access shim 2024. The shim layer 2024 receives the code and redirects and/or performs an appropriate action to retrieve, store, and/or operate on the data at the correct enterprise. As shown in the example of FIG. 20, the cross-enterprise data access shim 2024 sits above a plurality of participating enterprises A-C providing data access 2030-2032. The shim 2024 determines an appropriate enterprise for data access 2030-2032 to the desired data 2040-2042.

Single Patient Jacket

Certain examples leverage a cross-enterprise, integrated implementation to provide a single patient jacket, which facilitates a single view of patient data across multiple imaging back ends and/or multiple enterprises. The single patient jacket enables a user participating in the cross-enterprise exchange to have a broad view of the patient through a single interface/application via the single patient jacket and integrated clinical system (e.g., rather than disconnected information and limited patient data).

Figure 21:
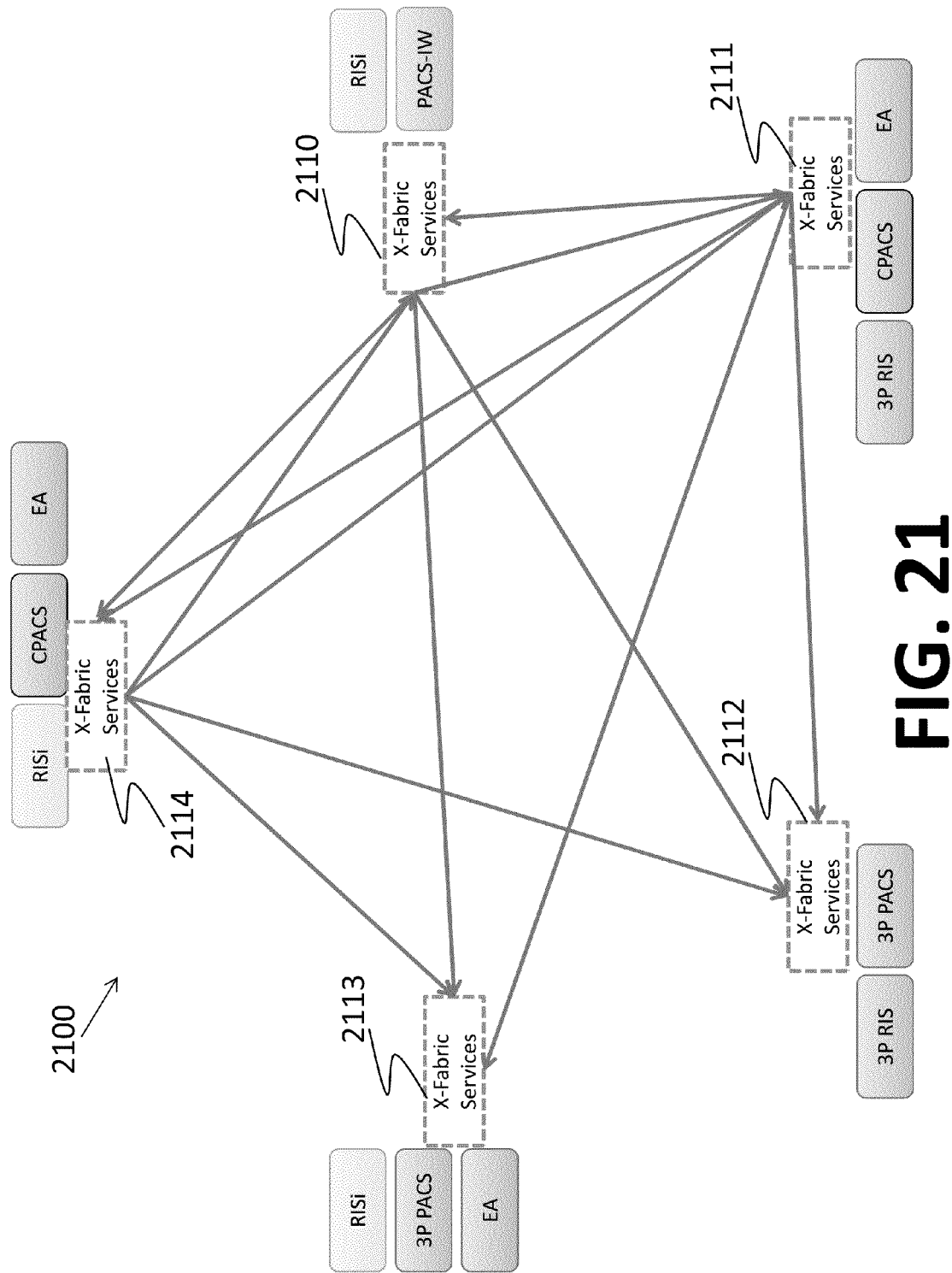
FIG. 21 shows an example of vendor neutral viewer via a decentralized model with a local data access deployment model.

FIG. 21 shows an example of vendor neutral viewing (VNV) via a decentralized model with a local data access deployment model 2100. In the example system 2100, data can be organized into a single patient jacket cross-enterprise through the use of cross-enterprise fabric services (XFS) 2110-2114 associated with each participating enterprise. As shown in the example of FIG. 21, each XFS 2110-2114 interfaces one or more local systems (e.g., RIS, PACS, EA, etc.) such that each enterprise can connect and interact with other participating enterprises to gather data for a patient and combine that data in presentation to a user in a single, global patient jacket/file/report.

Figure 22:
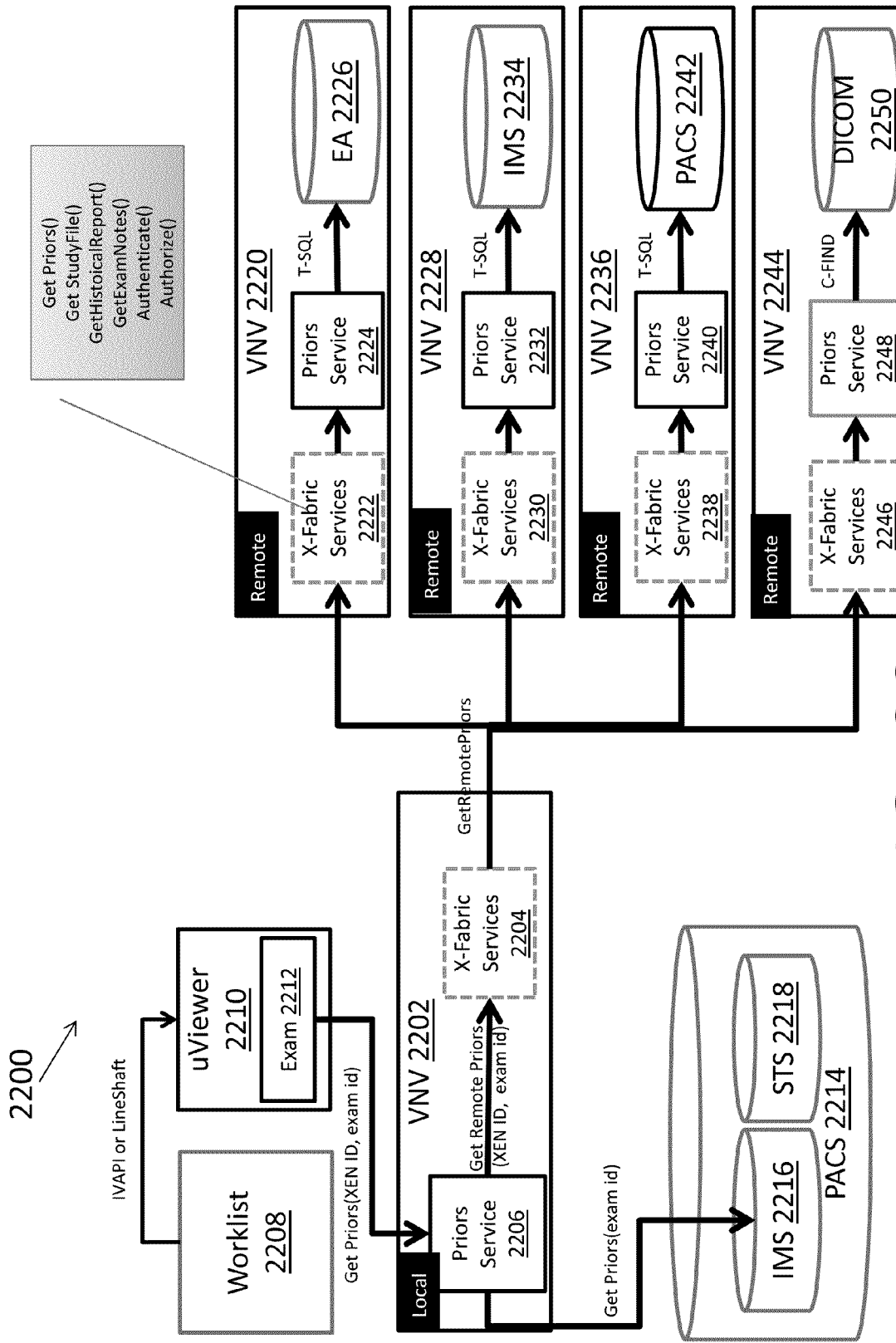
FIG. 22 illustrates an example vendor neutral viewer of global priors for a patient.

FIG. 22 illustrates an example vendor neutral viewer 2200 of global priors for a patient. The example system 2200 includes a local VNV 2202 including a priors service 2206 and cross-enterprise fabric services (XFS) 2204. The priors service 2206 uses the XFS 2204 to get priors from one or more remote systems based on a cross-enterprise ID and an exam ID, for example. Thus, a user can select an exam from a worklist 2208 to pull up the exam 2212 in a viewer 2210. The viewer 2210 contacts the local priors service 2206 to get priors for display, including local and remote priors, where applicable.

Local priors are retrieved via the priors service 2206 from a local PACS 2214, which can include an image management system (IMS) 2216 and short term storage 2218 (STS), for example. The IMS 2216 can include a database storing persistent data for exams, images, etc., stored in the PACS 2214. The STS 2218 can be used to store images temporarily in a fast disk-based cache (as opposed to long term on a tape library), for example.

Remote priors are requested using the XFS 2204, which communicates with one or more participating remote VNVs 2220, 2228, 2236, 2244. Each remote VNV 2220, 2228, 2236, 2244 includes its own XFS 2222, 2230, 2238, 2246, priors service 2224, 2232, 2240, 2248 and associated storage (e.g., EA 2226, IMS 2234, PACS 2242, DICOM 2250) from which to identify and, if applicable, retrieve priors (e.g., based on availability, authentication, authorization, etc.). As depicted in the example of FIG. 22, the XFS 2222 receives a request to get priors (and, alternatively or in addition, getting an associated study file, getting a historical reporting, getting exam notes, etc.) as well as authentication and authorization of the requesting user/enterprise. Retrieved priors are then sent back to the requesting XFS 2204 and/or access to the remote priors is provided for display via the viewer 2210.

Figure 23:
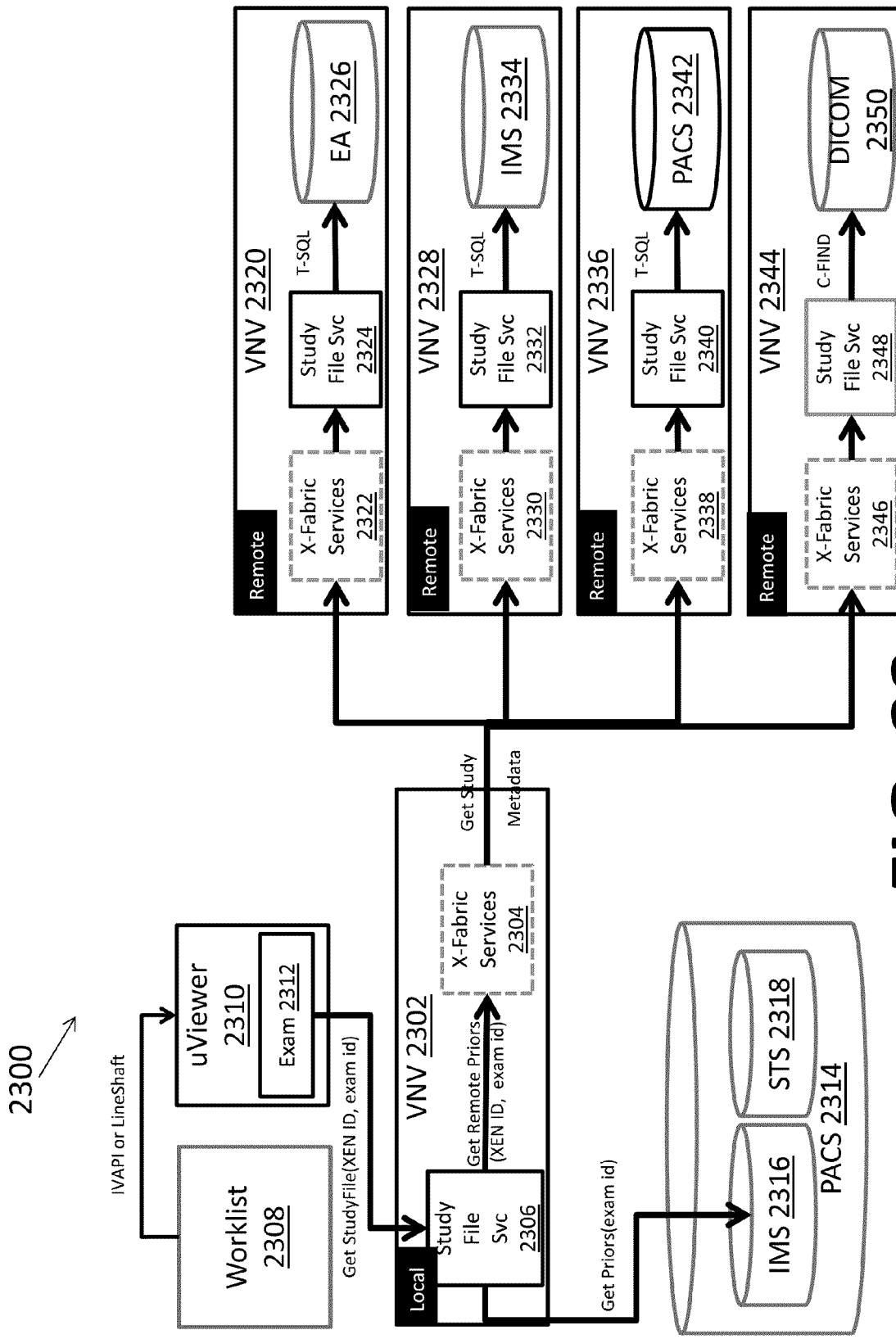
FIG. 23 illustrates an example vendor neutral viewer of a study file.

FIG. 23 illustrates an example vendor neutral viewer 2300 of a study file. The example system 2300 can be the same and/or similar to the example system 2200, for example, but illustrated using a study file rather than image, for example. The example system 2300 includes a local VNV 2302 including a study file service 2306 and cross-enterprise fabric services 2304. The study file service 2306 uses the XFS 2304 to get the requested study file contents from one or more remote systems based on a cross-enterprise ID and an exam ID, for example. Thus, a user can select an exam from a worklist 2308 to pull up the exam 2312 in a viewer 2310 as part of the global priors display.

The viewer 2310 contacts the local study file service 2306 to get study file content for display, including local and remote study file content, where applicable. Local study file content is retrieved via the priors service 2306 from a local PACS 2314, which can include an image management system (IMS) 2316 and short term storage 2318 (STS), for example.

Remote priors are requested using the XFS 2304, which communicates with one or more participating remote VNVs 2320, 2328, 2336, 2344. Each remote VNV 2320, 2328, 2336, 2344 includes its own XFS 2322, 2330, 2338, 2346, study file service 2324, 2332, 2340, 2348 and associated storage (e.g., EA 2326, IMS 2334, PACS 2342, DICOM 2350) from which to identify and, if applicable, retrieve study file information (e.g., based on availability, authentication, authorization, etc.). As depicted in the example of FIG. 23, the XFS 2322 receives a request for study metadata, for which it contacts its study file service 2324 to retrieve study information from the EA 2326. Retrieved study information is then sent back to the requesting XFS 2304 and/or access to the remote study data is provided for display via the viewer 2310 as part of the global study file.

Figure 24:
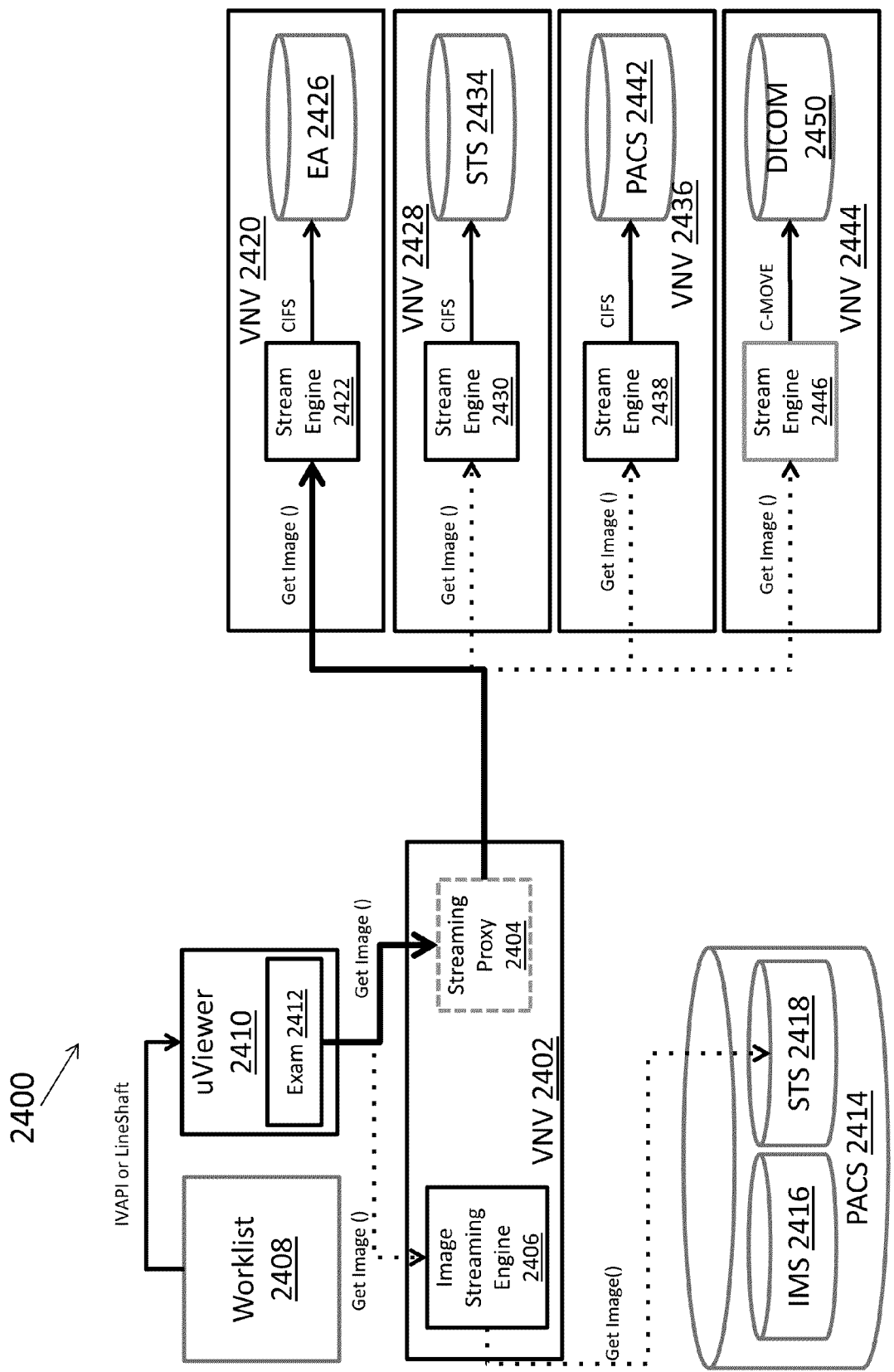
FIG. 24 illustrates an example vendor neutral viewer of image access.

FIG. 24 illustrates an example vendor neutral viewer 2400 of image access. The example system 2400 can be the same and/or similar to the example system 2200 and/or 2300, for example, but illustrated using a request for image access rather than image, for example. The example system 2400 includes a local VNV 2402 including an image streaming engine 2406 and a streaming engine proxy 2404. A user can select an exam from a worklist 2408 to pull up the exam 2412 in a viewer 2410 as part of an image display.

The viewer 2410 contacts the local image streaming engine 2406 to get local image content for display, which is retrieved from a local PACS 2414, which can include an image management system (IMS) 2416 and short term storage 2418 (STS), for example.

Remote image(s) are requested by the viewer 2410 using the streaming engine proxy 2404, which communicates with one or more participating remote VNVs 2420, 2428, 2436, 2444. Each remote VNV 2420, 2428, 2436, 2444 includes its own image streaming engine 2422, 2430, 2438, 2446 and associated storage (e.g., EA 2426, STS 2434, PACS 2442, DICOM 2450) from which to identify and, if applicable, retrieve image(s) (e.g., based on availability, authentication, authorization, etc.). As depicted in the example of FIG. 24, the image streaming engine 2422 receives a request for an image, which it retrieves from the EA 2426 provides to the proxy 2404 and/or otherwise enables access to the remote image via the viewer 2410.

Deployment Examples

Certain examples facilitate deployment of an integrated, gross enterprise solution in one or more ways. For example, cross-enterprise global reading may be delivered only to other participating integrated systems. All participating enterprises run their workflow and imaging using the integrated clinical information system solution.

Alternatively or in addition, one or more integrated systems can front non-integrated workflow and/or imaging systems such that participating, integrated enterprises can continue to run legacy systems for workflow and imaging while networking cross-enterprise using the integrated systems. In certain examples, no MFD synch-up is required over the cross-enterprise grid to allow the various types of systems to inter-operate. No patient, order, or image data is stored permanently outside of the enterprise from which it originated. Variation in capability of external RIS, PACS, and/or other system can be handled at a local enterprise level.

Thus, data duplication can be avoided between enterprises in the cross-enterprise framework, while individual enterprises retain complete control over security/access, patient and exam data, etc. Enterprises have freedom to join and leave the cross-enterprise arrangement without leaving behind traces of local enterprise data, for example.

Example Methods for Cross-Enterprise Reference Sharing and Resolution

While example implementations are disclosed and described above with respect to FIGS. 1-24, one or more of the elements, processes and/or devices illustrated in FIGS. 1-24 may be combined, divided, re-arranged, omitted, eliminated and/or implemented in any other way. Further, one or more elements of systems and configurations disclosed and described herein may be implemented by hardware, software, firmware and/or any combination of hardware, software and/or firmware. Thus, for example, any of the example elements shown in FIGS. 1-24 can be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example components is/are hereby expressly defined to include a tangible computer readable storage device or storage disk such as a memory, a digital versatile disk (DVD), a compact disk (CD), a Blu-ray disk, etc. storing the software and/or firmware. Further still, example systems and configurations may include one or more elements, processes and/or devices in addition to, or instead of, those illustrated in FIGS. 1-24, and/or may include more than one of any or all of the illustrated elements, processes and devices.

Figure 25:
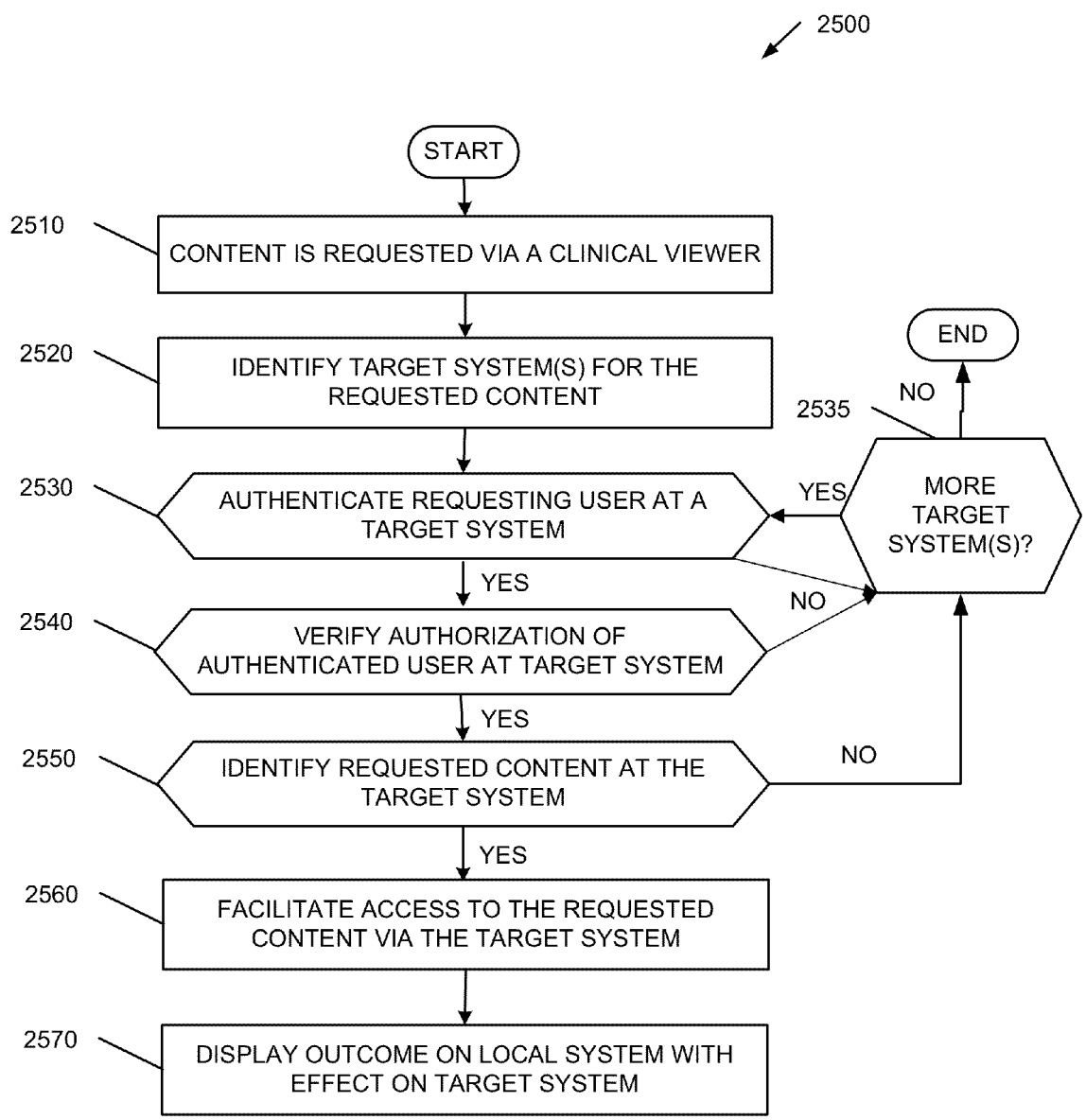
FIG. 25 is a flow diagram representative of example computer/machine readable instructions that may be executed to implement the example systems and configurations disclosed and described with respect to FIGS. 1-24.

FIG. 25 is a flow diagram representative of example computer/machine readable instructions that may be executed to implement the example systems and configurations disclosed and described with respect to FIGS. 1-24. In this example, the computer/machine readable instructions include a program for execution by a processor such as the processor 2612 shown in the example processor platform 2600 discussed below in connection with FIG. 26. The program may be embodied in software stored on a tangible computer readable storage medium such as a CD-ROM, a floppy disk, a hard drive, a digital versatile disk (DVD), a Blu-ray disk, or a memory associated with the processor 2612, but the entire program and/or parts thereof could alternatively be executed by a device other than the processor 2612 and/or embodied in firmware or dedicated hardware. Further, although an example program is described with reference to the flowchart illustrated in FIG. 25, many other methods of implementing the example systems, dashboards, etc., may alternatively be used. For example, the order of execution of the blocks may be changed, and/or some of the blocks described may be changed, eliminated, or combined.

As mentioned above, the example process(es) of FIG. 25 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of FIG. 25 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Although the following examples are described in conjunction with the example systems and configurations of FIGS. 1-24, the example method 2500 may be used in conjunction with other information systems. FIG. 25 illustrates a flow diagram of an example method 2500 to facilitate cross-enterprise access to information and functionality while maintain separation and control between enterprises by distinguishing between local and remote references.

At block 2510, content is requested via a clinical viewer. For example, a user at a clinical viewer can select an exam from his or her worklist to open a study file, retrieve one or more exams, schedule an appointment, read and report on an image, etc. At block 2520, one or more appropriate target systems are identified as at least potential source(s) for the requested content. For example, a manager, service, proxy, and/or director associated with a local system identifies one or more remote systems, connected through the cross-enterprise, which, instead of or in addition to the local system, include information relevant to the request.

At block 2530, the requesting user is authenticated at the local system. For example, using Active Directory, SSO, LDAP, etc., the local system verifies that the requesting user is who he/she/it says it is. If the requesting user is validated, then, at block 2540, a target system (local and/or remote) identified as including relevant information verifies that the authenticated requesting user is authorized to obtain, view, access, etc., that information at its system. Thus, a user who has been authenticated is verified by a remote system to confirm that such a user (or that particular user, in fact) is authorized (e.g., has permission) to access the information (e.g., receive it, view it, interact with it, etc.).

If the authenticated user is authorized, then, at block 2550, the requested content is identified at the target system. For example, one or more services, proxy, etc., at a target system determine whether or not the relevant content (e.g., data, application, other functionality, etc.) is in fact found at the target system. If so, then, at block 2560, the user at the local system accesses the requested content via the target system. Thus, if the requested data and/or functionality is found at the local system, then the data is displayed and/or application is executed by the user at the local system. If, however, the requested data and/or functionality is found at a remote system, then the data is displayed and/or application is executed at the remote system but provided to the user via the local viewer. Thus, rather than creating local copies and/or providing content for local viewing/interaction/execution, the requested action can occur on the content's native system (local and/or remote), allowing the host system to maintain control while still facilitating sharing and collaboration cross-enterprise. At block 2570, an outcome is displayed at the local system while any effect occurs at the target system. Thus, as described above, while the user sees the requested content and/or a result of interaction with that content at his/her/its local system, any update, modification, or effect occurs at the content's host system, which may be the user's local system and/or a remote system that is part of the cross-enterprise configuration. At block 2535, the process can repeat according to a number of identified target systems.

Figure 26:
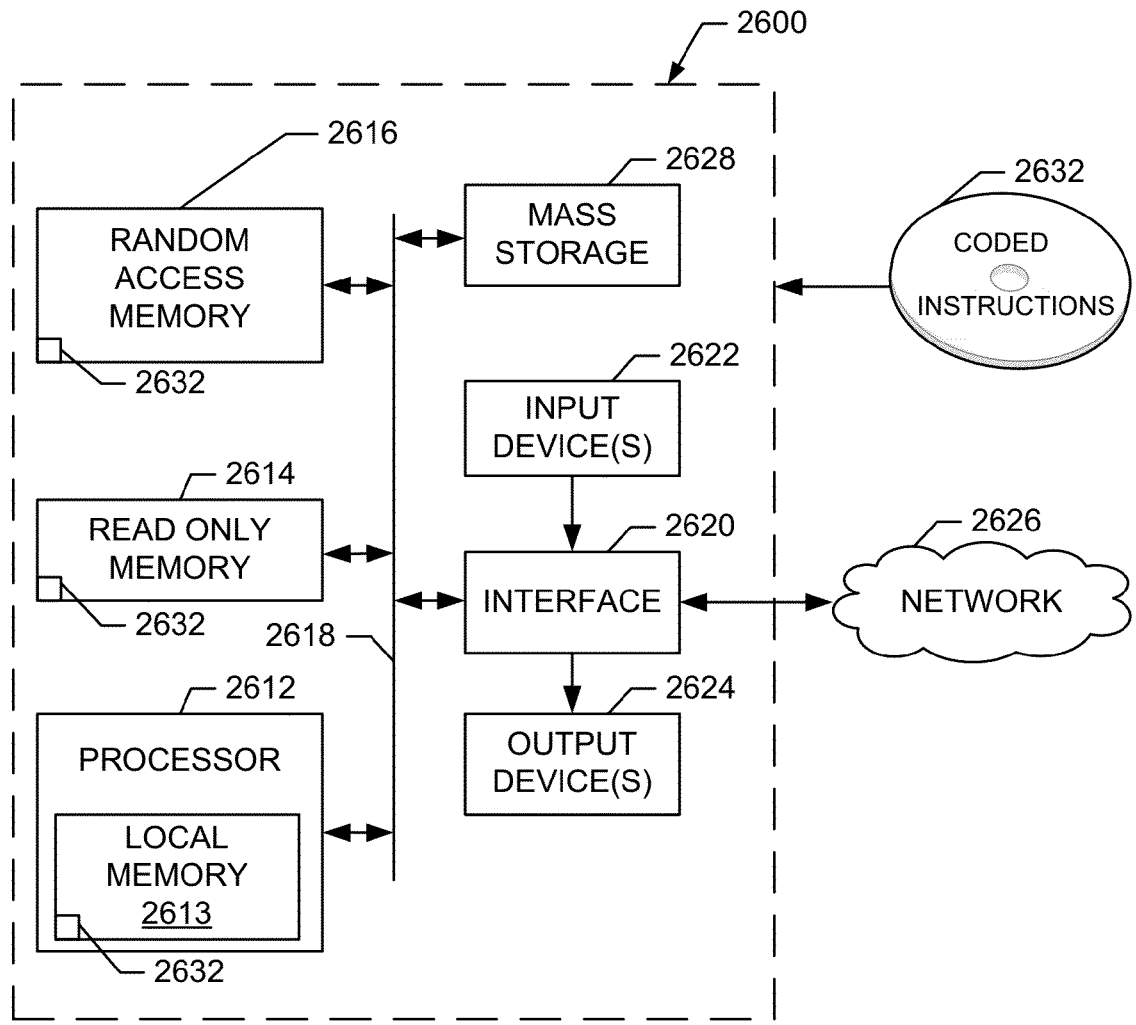
FIG. 26 is a block diagram of an example processing platform capable of executing the example computer/machine readable instructions and/or to implement the example systems of FIGS. 1-25.

FIG. 26 is a block diagram of an example processor platform 2600 capable of executing the instructions of FIG. 25 and/or to implement the example systems and configurations of FIGS. 1-24. The processor platform 2600 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 2600 of the illustrated example includes a processor 2612. The processor 2612 of the illustrated example is hardware. For example, the processor 2612 can be implemented by one or more integrated circuits, logic circuits, microprocessors or controllers from any desired family or manufacturer.

The processor 2612 of the illustrated example includes a local memory 2613 (e.g., a cache). The processor 2612 of the illustrated example is in communication with a main memory including a volatile memory 2614 and a non-volatile memory 2616 via a bus 2618. The volatile memory 2614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2616 may be implemented by flash memory and/or any other desired type of memory device. Access to the main memory 2614, 2616 is controlled by a memory controller.

The processor platform 2600 of the illustrated example also includes an interface circuit 2620. The interface circuit 2620 may be implemented by any type of interface standard, such as an Ethernet interface, a universal serial bus (USB), and/or a PCI express interface.

In the illustrated example, one or more input devices 2622 are connected to the interface circuit 2620. The input device(s) 2622 permit(s) a user to enter data and commands into the processor 2612. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2624 are also connected to the interface circuit 2620 of the illustrated example. The output devices 2624 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 2620 of the illustrated example, thus, typically includes a graphics driver card, a graphics driver chip or a graphics driver processor.

The interface circuit 2620 of the illustrated example also includes a communication device such as a transmitter, a receiver, a transceiver, a modem and/or network interface card to facilitate exchange of data with external machines (e.g., computing devices of any kind) via a network 2626 (e.g., an Ethernet connection, a digital subscriber line (DSL), a telephone line, coaxial cable, a cellular telephone system, etc.).

The processor platform 2600 of the illustrated example also includes one or more mass storage devices 2628 for storing software and/or data. Examples of such mass storage devices 2628 include floppy disk drives, hard drive disks, compact disk drives, Blu-ray disk drives, RAID systems, and digital versatile disk (DVD) drives.

The coded instructions 2632 (e.g., of FIG. 25) may be stored in the mass storage device 2628, in the volatile memory 2614, in the non-volatile memory 2616, and/or on a removable tangible computer readable storage medium such as a CD or DVD.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A cross-enterprise enabled clinical information system comprising:
    a hardware processor specially configured to implement the cross-enterprise enabled clinical information system including:
    a workflow manager implemented by the processor to coordinate user workflows with respect to the clinical information system and associated content; and
    an image services manager implemented by the processor and configured to manage images and associated services for the clinical information system and associated content,
    wherein the workflow manager and image services manager are configured for cross-enterprise content sharing such that the clinical information system is to locally authenticate a local user at the clinical information system and the clinical information system is to locally authorize a remote request for access to content at the clinical information system from a remote user that has been authenticated remotely by a remote system of the remote user, the clinical information system arranged to provide content in response to the remote request after the remote authentication has been received and the clinical information system has verified the remote user's authorization for access, at least one of the workflow manager and the image services manager providing content to the remote user from the clinical information system depending upon a type of requested content,
    wherein, when content is provided via the clinical information system to the system of the remote user in response to the remote request, no historical patient data is to be transferred for persistence at the remote system.

2. The system of claim 1, further comprising a cross-enterprise data access shim to transparently intercept the remote request for content and a least one of change and redirect the request among a plurality of systems participating in the cross-enterprise content sharing.

3. The system of claim 1, further comprising cross-enterprise fabric services to facilitate a request for content from one or more remote systems by a local user at the clinical information system.

4. The system of claim 1, wherein no master file data synchronization is performed with the remote request for access to content.

5. The system of claim 1, wherein the workflow manager and the image services manager share at least one of study file and hanging protocol management, exception management, collaboration, and information prefetch.

6. The system of claim 1, wherein the workflow manager is configure to interact with one or more of an electronic medical record, an electronic health record, a hospital information system, and a radiology information system.

7. The system of claim 1, wherein the image services manager is configured to interact with one or more of a vendor neutral archive, a picture archiving and communication system, and an imaging modality.

8. The system of claim 1, wherein the workflow manager and image services manager are configured to gather information regarding a patient from the clinical information system and one or more remote systems to form a single patient jacket for review by a user.

9. The system of claim 1, wherein the workflow manager and image services manager are configured to gather information regarding user's worklist from the clinical information system and one or more remote systems to form a global reading worklist for review by the user.

10. A tangible computer readable storage device including instructions which, when executed, specially configure a hardware processor to implement a cross-enterprise enabled clinical information system, the system comprising:

a workflow manager implemented by the processor to coordinate user workflows with respect to the clinical information system and associated content; and an image services manager implemented by the processor and configured to manage images and associated services for the clinical information system and associated content, wherein the workflow manager and image services manager are configured for cross-enterprise content sharing such that the clinical information system is to locally authenticate a local user at the clinical information system and the clinical information system is to locally authorize a remote request for access to content at the clinical information system from a remote user that has been authenticated remotely by a remote system of the remote user, the clinical information system arranged to provide content in response to the remote request after the remote authentication has been received and the clinical information system has verified the remote user's authorization for access, at least one of the workflow manager and the image services manager providing content to the remote user from the clinical information system depending upon a type of requested content, wherein, when content is provided via the clinical information system to the system of the remote user in response to the remote request, no historical patient data is to be transferred for persistence at the remote system.

11. The storage device of claim 10, further comprising a cross-enterprise data access shim to transparently intercept the remote request for content and a least one of change and redirect the request among a plurality of systems participating in the cross-enterprise content sharing.

12. The storage device of claim 10, further comprising cross-enterprise fabric services to facilitate a request for content from one or more remote systems by a local user at the clinical information system.

13. The storage device of claim 10, wherein no master file data synchronization is performed with the remote request for access to content.

14. The storage device of claim 10, wherein the workflow manager and the image services manager share at least one of study file and hanging protocol management, exception management, collaboration, and information prefetch.

15. The storage device of claim 10, wherein the workflow manager is configure to interact with one or more of an electronic medical record, an electronic health record, a hospital information system, and a radiology information system.

16. The storage device of claim 10, wherein the image services manager is configured to interact with one or more of a vendor neutral archive, a picture archiving and communication system, and an imaging modality.

17. The storage device of claim 10, wherein the workflow manager and image services manager are configured to gather information regarding a patient from the clinical information system and one or more remote systems to form a single patient jacket for review by a user.

18. The storage device of claim 10, wherein the workflow manager and image services manager are configured to gather information regarding user's worklist from the clinical information system and one or more remote systems to form a global reading worklist for review by the user.

* * * * *